United States Patent
Liu

(10) Patent No.: US 10,117,874 B2
(45) Date of Patent: Nov. 6, 2018

(54) COMBINATION OF PI3K-INHIBITORS

(71) Applicant: BAYER PHARMA AKTIENGESELLSCHAFT, Berlin (DE)

(72) Inventor: Ningshu Liu, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/101,638

(22) PCT Filed: Nov. 28, 2014

(86) PCT No.: PCT/EP2014/075886
§ 371 (c)(1),
(2) Date: Jun. 3, 2016

(87) PCT Pub. No.: WO2015/082322
PCT Pub. Date: Jun. 11, 2015

(65) Prior Publication Data
US 2016/0303136 A1 Oct. 20, 2016

(30) Foreign Application Priority Data
Dec. 3, 2013 (EP) .................................... 13195485

(51) Int. Cl.
| | | |
|---|---|---|
| A61K 9/00 | (2006.01) | |
| A61K 31/5377 | (2006.01) | |
| A61K 45/06 | (2006.01) | |
| A61K 51/02 | (2006.01) | |
| A61K 31/519 | (2006.01) | |
| A61K 33/14 | (2006.01) | |
| A61K 51/00 | (2006.01) | |
| A61K 51/04 | (2006.01) | |

(52) U.S. Cl.
CPC ........ *A61K 31/5377* (2013.01); *A61K 31/519* (2013.01); *A61K 33/14* (2013.01); *A61K 45/06* (2013.01); *A61K 51/02* (2013.01); *A61K 51/00* (2013.01); *A61K 51/04* (2013.01)

(58) Field of Classification Search
None
See application file for complete search history.

(56) References Cited

U.S. PATENT DOCUMENTS

| | | |
|---|---|---|
| 6,635,234 B1 | 10/2003 | Larsen et al. |
| 8,142,758 B2 | 3/2012 | Larsen et al. |
| 8,926,943 B2 | 1/2015 | Karlson et al. |
| 9,056,142 B2 | 6/2015 | Karlson et al. |
| 9,173,814 B2 | 11/2015 | Jakobsen et al. |

FOREIGN PATENT DOCUMENTS

| | | |
|---|---|---|
| WO | 2008/070150 A1 | 6/2008 |
| WO | 2012/062743 A1 | 5/2012 |
| WO | 2012/062745 A1 | 5/2012 |
| WO | 2012/062748 A1 | 5/2012 |

OTHER PUBLICATIONS

M.D. Wissing et al: "Radium-223 Chloride: Extending Life in Prostate Cancer Patients by Treating Bone Metastases", Clinical Cancer Research, vol. 19, No. 21, Sep. 19, 2013 (Sep. 19, 2013), pp. 5822-5827.
Jayant K. Rane et al: "Advanced prostate cancer—a case for adjuvant differentiation therapy", Nature Reviews Urology, vol. 9, No. 10, Aug. 14, 2012( Aug. 14, 2012), pp. 595-602.
J. M. Clarke Et Al: "Novel Therapies for the Treatment of Advanced Prostate Cancer", Current treatment Options in Oncology, vol. 14, No. 1, Jan. 16, 2013 (Jan. 16, 2013), pp. 109-126.
Co-pending U.S. Appl. No. 14/548,599, filed Nov. 20, 2014.
Co-pending U.S. Appl. No. 14/912,312, filed Feb. 16, 2016.
Co-pending U.S. Appl. No. 14/654,053, filed Jun. 19, 2015.
International Search Report, PCT/EP2014/075886, dated Jan. 15, 2015.
Co-pending U.S. Appl. No. 15/101,540, filed Jun. 3, 2016.

*Primary Examiner* — James W Rogers
(74) *Attorney, Agent, or Firm* — Morrison & Foerster LLP

(57) ABSTRACT

The present invention relates to combinations of at least two components, component A and component B, component A being an inhibitor of PI3K kinase, and component B being radium 223, particularly a pharmaceutically acceptable salt of radium-223. Another aspect of the present invention relates to the use of such combinations as described herein for the preparation of a medicament for the treatment or prophylaxis of a disease, particularly for the treatment of breast and prostate cancer as well as their bone metatases.

14 Claims, 4 Drawing Sheets

A : The effects of compound A' and compound B on MCF-7 breast tumor cell proliferation at days 1-5 (A) and B : Apoptosis induction at day 2.

The effects of compound A' and compound B on 4T1 cell proliferation at days 1-5.

The effects of compound A' and compound B on PC3 cell proliferation at days 1-5.

A :

B :

A : The effects of compound A' and compound B on LNCaP cell proliferation at days 1-5 (A) and B : Apoptosis induction at day 5.

COMBINATION OF PI3K-INHIBITORS

CROSS REFERENCE TO RELATED APPLICATIONS

This application is a National Phase application under 35 U.S.C. § 371 of International Application No. PCT/EP2014/075886, filed Nov. 28, 2014, which claims priority benefit of European Application No. 13195485.1, filed Dec. 3, 2013.

The present invention relates to combinations of at least two components, component A and component B, component A being a PI3K-inhibitor, and component B being a pharmaceutically acceptable salt of the alkaline-earth radionuclide radium-223.

Another aspect of the present invention relates to the use of such combinations as described herein for the preparation of a medicament for the treatment or prophylaxis of a disease, particularly for the treatment of cancer.

Yet another aspect of the present invention relates to methods of treatment or prophylaxis of a cancer in a subject, comprising administering to said subject a therapeutically effective amount of a combination as described herein.

Further, the present invention relates to a kit comprising a combination of:
- one or more components A, as defined herein, or a physiologically acceptable salt, solvate, hydrate or stereoisomer thereof;
- a component B, as defined supra, or a solvate or hydrate thereof; and, optionally
- one or more pharmaceutical agents C;

in which optionally either or both of said components A and B are in the form of a pharmaceutical formulation which is ready for use to be administered simultaneously, concurrently, separately or sequentially.

Component A may be administered by the oral, intravenous, topical, local installations, intraperitoneal or nasal route.

Component B preferably is administered by the intravenous route.

BACKGROUND TO THE INVENTION

Cancer is the second most prevalent cause of death in the United States, causing 450,000 deaths per year. While substantial progress has been made in identifying some of the likely environmental and hereditary causes of cancer, there is a need for additional therapeutic modalities that target cancer and related diseases. In particular there is a need for therapeutic methods for treating diseases associated with dysregulated growth/proliferation.

Cancer is a complex disease arising after a selection process for cells with acquired functional capabilities like enhanced survival/resistance towards apoptosis and a limitless proliferative potential. Thus, it is preferred to develop drugs for cancer therapy addressing distinct features of established tumors.

The PI3K/AKT/mTOR pathway, which is constitutively activated in many types of cancers, is one of the prominent pathway that promote tumor cell survival. Initial activation of the PI3K/AKT/mTOR pathway occurs at the cell membrane, where the signal for pathway activation is propagated through class IA PI3K. Activation of PI3K can occur through tyrosine kinase growth factor receptors (e.g. platelet-derived growth factor receptor (PDGF-R), human epidermal growth factor 1/2/3 receptor (EGFR, HER2/3), or the insulin-like growth factor 1 receptor (IGF-1R)), cell adhesion molecules through integrin-linked kinase (ILK), Ca2+/calmodulin-dependent kinase kinase (CaMKK), nuclear DNA-dependent protein kinase (DNA-PK), G-protein-coupled receptors, and oncogenic proteins, such as Ras. Once PI3K is activated, it catalyzes phosphorylation of the D-3 position on phosphoinositides to generate the biologically-active phosphatidylinositol-3,4,5-triphosphate [PI(3,4,5)P$_3$, PIP$_3$] and phosphatidylinositol-3,4-bisphosphate [PI(3,4)P$_2$, PIP$_2$]. PIP$_3$ binds to the pleckstrin homology (PH) domains of phosphoinositide-dependent kinase 1 (PDK-1), AKT, and other PH-domain containing proteins, such as Rho and PLC. As the consequence of binding to PIP$_3$, the proteins are translocated to the cell membrane and are subsequently activated. The tumour suppressor PTEN (phosphatase and tensin homolog deleted on chromosome 10) antagonizes PI3K by dephosphorylating PIP$_3$, thereby preventing translocation and activation of PDK1, AKT and other signaling proteins.[1,2]

AKT is the major effecter of PI3K, which elicits a broad range of downstream signaling events. It recognizes and phosphorylates the consensus sequence RXRXX(S/T) when surrounded by hydrophobic residues. As this sequence is present in many proteins, about 50 AKT substrates have been identified and validated.[3,4] These substrates control key cellular processes such as apoptosis, cell cycle progression, transcription, and translation, stress adaptation, metabolism, and metastasis of tumor cells. For instance, AKT phosphorylates the FOXO subfamily of forkhead family transcription factors, which inhibits transcription of several pro-apoptotic genes, e.g. Fas-L, IGFBP1 and Bim.[5,6] Additionally, AKT can directly regulate apoptosis by phosphorylating and inactivating pro-apoptotic proteins such as Bad, which control the release of cytochrome c from mitochondria, and apoptosis signal-regulating kinase-1, a mitogen-activated protein kinase kinase involved in stress-induced and cytokine-induced cell death.[7] In contrast, AKT can phosphorylate IκB kinase, which indirectly increases the activity of nuclear factor KB and stimulates the transcription of pro-survival genes.[8] Cell cycle progression can also be affected at the G1/S transition by AKT through its inhibitory phosphorylation of the cyclin dependent kinase inhibitors, p21WAF1/CIP1 and p27KIP1. In addition AKT can phosphorylate mouse double minute 2 (MDM2) leading to its nuclear translocation and promotion of degradation of p53. This in consequence leads to an decrease in p21Cip1mRNA.[9] Furthermore AKT has also an important function in the control of the G2/M transition by e.g. phosphorylation of Myt1 and FOX03a.[10,11]

The best-studied downstream substrate of AKT is the serine/threonine kinase mTOR. AKT can directly phosphorylate and activate mTOR, as well as cause indirect activation of mTOR by phosphorylating and inactivating TSC2 (tuberous sclerosis complex 2, also called tuberin), which normally inhibits mTOR through the GTP-binding protein Rheb (Ras homolog enriched in brain). When TSC2 is inactivated by phosphorylation, the GTPase Rheb is maintained in its GTP-bound state, allowing for increased activation of mTOR. mTOR exists in two complexes: the TORC1 complex, in which mTOR is bound to Raptor, and the TORC2 complex, in which mTOR is bound to Rictor.[12] In the TORC1 complex, mTOR phosphorylates its downstream effectors S6 kinase (S6K1) and 4EBP-1. S6K1 can then phosphorylate its substrate, a ribosomal protein called S6. 4EBP-1, when phosphorylated cannot bind effectively to its binding partner, eIF4E. The cumulative effect is to increase protein translation, especially of highly structured, capped mRNA species.[13] Although mTOR is generally considered a downstream substrate of AKT, mTOR in complex with Rictor can also phosphorylate AKT at S473, thereby providing a level of positive feedback on the pathway.[14] Finally, S6K1 can also regulate the pathway by catalyzing an inhibitory phosphorylation on insulin receptor substrate proteins (IRS). This prevents IRS from activating PI3K, which indirectly lowers activation of AKT. This feedback pathway is very important for developing PI3K/AKT/mTOR pathway inhibitors, as the re-activation of PI3K has to be taken into consideration during the evaluation of the anti-tumor efficacy of the PI3K pathway inhibitors.[15,16]

In addition to the well described PI3K/AKT/mTOR axis of the PI3K signaling pathway, PI3K, AKT and mTOR also receive and branch differential signaling events that are independent from the axis. For example, mTOR has the crosstalk with and is activated by MAPK pathway through ERK and RSK regulated phosphorylation of TSC2.[17] There are collective data describing the AKT/mTOR-independent PI3K-mediated signaling events. First of all, PI3K downstream signaling molecule PDK1 responses to increased levels of PIP3 and activates not only AKT, but also a group of AGC kinases comprising S6K, RSK, SGK and PKC isoforms, which play essential roles in regulating tumor cell growth, proliferation, survival and metabolism.[18] Furthermore, many PIK3CA mutant cancer cell lines and human breast tumors exhibit only minimal AKT activation and a diminished reliance on AKT for anchorage-independent growth. Instead, these cells retain robust PDK1 activation and membrane localization and exhibit dependency on the PDK1 substrate SGK3. SGK3 undergoes PI3K- and PDK1-dependent activation in PIK3CA mutant cancer cells. Thus, PI3K may promote cancer through both AKT-dependent and AKT-independent mechanisms.[19] In addition to PDK1 and AGC kinases, PI3Ks regulate also other cancer related signaling proteins such as PLC, Rac, Rho, ITK and BTK, etc.

In humans, class I PI3K has four isoforms of the p110 catalytic subunits, p110α, p110β, p110γ and 110δ. p110α and p110β are present in all cell types, while p110δ and p110γ are highly enriched in leukocytes. p110 subunits are divided into a class IA group (p110α, p110β and p110δ), which bind the p85 regulatory subunit, and a class IB group (p110γ), which does not. The p85 regulatory subunits contain Src homology 2 (SH2) domains and bind phosphorylated tyrosine (pTyr), which lead to the activation of the class IA p110 catalytic subunits. On the other hand, p110γ is activated directly through G protein coupled receptors (GPCRs). Recent data indicated that p110? was also activated by GPCRs directly through Gβγ protein.[20]

The signaling inputs to each class I PI3Ks are diverse and well depicted in genetic analyses. Thus, activation of AKT was impaired in p110α-deficient MEFs upon stimulation by classical RTK ligands (EGF, insulin, IGF-1, and PDGF).[21] On the other hand, MEFs in which p110β is ablated or replaced by a kinase-dead allele of p110β respond normally to growth factor stimulation via RTKs.[22] Instead, p110•catalytic activity is actually required for AKT activation in response to GPCR ligands (such as LPA). As such, p110α appears to carry the majority of the PI3K signal in classic RTK signaling and is responsible for tumor cell growth, proliferation, survival, angiogenesis and metabolism whereas p110β mediates GPCR signaling from mitogens and chemokines and therefore may regulate tumor cell proliferation, metabolism, inflammation and invasion.[23, 24]

Although the differences in signaling outputs from the four class I PI3K isoforms are still largely unknown, it seems that PI3K13 together with PTEN determines the basal levels of PIP3 in tumor cells, while RTK stimulated elevation of PIP3 is controlled mainly by PI3Kα. The potential for differential signaling outputs downstream of specific PI3K isoforms, in parallel with a possibly more universal Akt activation are yet to be discovered.

Activation of PI3K/AKT kinases promotes increased nutrient uptake, converting cells to a glucose-dependent metabolism that redirects lipid precursors and amino acids to anabolic processes that support cell growth and proliferation. These metabolic phenotype with overactivated AKT lead to malignancies that display a metabolic conversion to aerobic glycolysis (the Warburg effect). In that respect the PI3K/AKT pathway is discussed to be central for survival despite unfavourable growth conditions such as glucose depletion or hypoxia.

A further aspect of the activated PI3K/AKT pathway is to protect cells from programmed cell death ("apoptosis") and is hence considered to transduce a survival signal. By acting as a modulator of anti-apoptotic signalling in tumor cells, the PI3K/AKT pathway, particular PI3K itself is a target for cancer therapy. Activated PI3K/AKT phosphorylates and regulates several targets, e.g. BAD, GSK3 or FKHRL1, that affect different signalling pathways like cell survival, protein synthesis or cell movement. This PI3K/AKT pathway also plays a major part in resistance of tumor cells to conventional anti-cancer therapies. Blocking the PI3K/AKT pathway could therefore simultaneously inhibit the proliferation of tumor cells (e.g. via the inhibition of the metabolic effect) and sensitize towards pro-apoptotic agents. PI3K inhibition selectively sensitized tumor cells to apoptotic stimuli like Trail, Campthothecin and Doxorubicin.

The resistance of many types of cancer to chemo- and targeted therapeutics represents the major hurdle in successful cancer treatment. Cancer cells can escape the effect of most commonly used drugs despite their different chemical structure and intracellular targets. Many mechanisms underlying the failure of therapeutic drugs have been well studied. Activation of PI3K/AKT pathway plays a key role in different cellular functions such as growth, migration, survival and differentiation. Data accumulated in the last decade have established that this pathway plays also a key role in resistance to both chemo-, radiation- and targeted therapeutics. Collective data describing constitutive or residual pathway activation in cells that have developed resistance to conventional chemotherapy and radiation, as well as to other targeted therapies such as EGFR antagonists. For example, experiments in doxorubicin-resistant CML cell lines demonstrated high levels of PI3K/AKT activity; importantly, doxorubicin resistance could be overcome by decreasing PI3K/AKT activity. Further experimental evidence was observed in two pancreatic cancer cell lines in which decreased levels of phosphorylated AKT can increase gemcitabine-induced apoptosis. Synergistic antitumor activity with cisplatin was also demonstrated in xenograft models of lung cancer.

The PI3K/AKT pathway is linked to resistance to both chemo- and targeted therapeutics. The Inhibition of PI3Kβ might present a promising strategy to overcome the resistance to radiation and DNA targeting therapy. Nuclear PI3Kb can induce nuclear AKT phosphorylated on both T308 and S473 in response to either IR or the DNA-damaging agent doxorubicin.

In summary, PI3K plays central role downstream of many cancer related signaling pathways that are critical for tumorigenesis, tumor growth/proliferation and survival, tumor cell adhesion, invation and metastasis, as well as tumor angiogenesis. In addition, gain-function mutation of PIK3CA is common in several human cancers and the link between tumor suppressor gene PTEN and PI3K13 has been observed in some tumors such as prostate cancer. An increased expression of the p110β and p110 δ isoforms has been observed in some colon and bladder tumors, and in glioblastoma. In addition, nuclear PI3Kβ plays roles in DNA synthesis and repair.[35] Furthermore, p110δ controls proliferation in acute myeloid leukemia (AML) and migration of breast cancer cells,[36] whereas p110γ plays roles in tumor angiogenesis, drug resistance of CML cells, and pancreatic tumor growth and survival.[37] Thus, developing PI3K inhibitors for treatment in mono- and combination therapy is a promising strategy to treat cancer and overcome cancer treatment resistance.

Thus inhibitors of PI3K represent valuable compounds that should complement therapeutic options not only as single agents but also in combination with other drugs, e.g. DNA targeting agent and radiation therapy.

Alpharadin (Xofigo) uses alpha radiation from radium-223 decay to kill cancer cells. Alpharadin targets to bone tissue by virtue of its chemical similarity to calcium. It has an effect over a range of 2-10 cells and causes less damage to surrounding healthy tissues compared to current radiation therapy based on beta or gamma radiation. Significant increase in median overall survival was demonstrated in Phase III clinical trials and Alpharadin (Xofigo) was approved as a treatment for castration-resistant prostate cancer (CRPC) patients with symptomatic bone metastases.

Different PI3K inhibitors are disclosed in e.g. WO2008/070150, WO2012/062743, WO2012/062745, WO2012/062748.

However, the state of the art does not disclose the combinations of the present invention comprising an inhibitor of PI3K kinase or a physiologically acceptable salt thereof and a pharmaceutically acceptable salt of the alkaline-earth radionuclide radium-223.

A preferred suitable pharmaceutically acceptable salt of radium-223 is the dichloride ($Ra^{223}Cl_2$).

Radium-223 dichloride is a novel, targeted alpha-emitter that selectively binds to areas of increased bone turnover in bone metastases and emits high-energy alpha-particles of extremely short (<100 μm) range[37]

It is the first targeted alpha-emitter approved for the treatment of prostate cancer with bone metastasis.

As a bone-seeking calcium mimetic, radium-223 is bound into newly formed bone stroma, especially within the microenvironment of osteoblastic or sclerotic metastases.[38]

The high-energy alpha-particle radiation induces mainly double-strand DNA breaks resulting in a potent and highly localized cytotoxic effect in the target areas containing metastatic cancer cells.[39]

The short path length of the alpha-particles also means that toxicity to adjacent healthy tissue and particularly the bone marrow may be reduced.[40]

Radium-223 has demonstrated a favorable safety profile, with minimal myelotoxicity, in phase 1 and 2 studies of patients with bone metastases.[41]

Phase 2 studies have shown that radium-223 reduces pain, improves disease-related biomarkers (e.g., bone alkaline phosphatase [ALP] and prostate-specific antigen [PSA]), and have suggested a survival benefit in patients with CRPC and bone metastases.[42,43] The ALSYMPCA (ALpharadin in SYMptomatic Prostate CAncer patients) trial provides proof of principle for the role of targeted alpha-emitters in oncology. In this trial, radium-223 significantly prolonged overall survival with a 30.5% reduction in risk of death compared with placebo in patients with CRPC (Castration Resistant Prostate Cancer) and bone metastases. Median survival with radium-223 was longer than placebo by 2.8 months. All main secondary efficacy endpoints were statistically significant and favored treatment with radium-223, including the clinically defined endpoint of time to first skeletal-related event, which was significantly prolonged in patients receiving radium-223.

A substantial percentage of cancer patients is affected by skeletal metastases. As many as 85% of patients with advanced lung, prostate and breast carcinoma develop bony metastases.[44] Bone metastases: Pathophysiology and management policy.). Established treatments such as hormone therapy, chemotherapy and external radiotherapy often causes temporary responses, but ultimately most bone cancer patients experience relapses.[45] There is thus a strong need for new therapies to relieve pain and slow down tumor progression.

$^{223}Ra$ is used as an α-emitting radiopharmaceutical for targeting of calcified tissues, e.g., bone surfaces and osseous tumor lesions. It can be suitable as a bone seeking radiopharmaceutical.

It thus may be used for prophylactic cancer treatment by delivering a focused dose to bone surfaces in patients with a high probability of having undetected micrometastases at bone surfaces. Another example of its potential use would be in the treatment of painful osseous sites.

The alkaline-earth radionuclide radium-223 is useful for the targeting of calcified tissues, e.g., bone and a physiological acceptable solution comprising $^{223}Ra$.

The alkaline-earth radionuclide radium-223 is suitable for the use of the nuclide as a cationic species and/or associated to a chelator or another form of a carrier molecule with affinity for calcified tissues. Thus may be combined with a chelator that can be subsequently conjugated to a molecule with affinity for calcified tissues. The effect of the radioisotope to generated by providing a cascade of α-particles on bone surfaces and/or in calcified tumors for the palliation of pain caused by various diseases and/or for the prophylactic use against possible minimal disease to the skeleton, and/or also for the therapeutic treatment of established cancer to the bone. The diseases where the radioisotopes could be used includes, but are not limited to skeletal metastases of prostate-, breast-, kidney- and lung cancer as well as primary bone cancer and also multiple myeloma.

SUMMARY OF THE INVENTION

Surprisingly it was observed that by administering a PI3K inhibitor or a physiologically acceptable salt, solvate, hydrate or stereoisomer thereof in combination with a suitable pharmaceutically acceptable salt of the alkaline-earth radionuclide radium-223 a synergistic anti-proliferative and apoptotic effects in breast and prostate tumor cell lines.

Therefore, in accordance with a first aspect, the present invention provides combinations of at least two components, component A and component B, component A being an inhibitor of PI3K-kinase (claim 1) or a physiologically acceptable salt, solvate, hydrate or stereoisomer thereof, and component B being a suitable pharmaceutically acceptable salt of the alkaline-earth radionuclide radium-223.

In accordance with a second aspect, (claim 2) the present invention covers combinations of at least two components A and B, component A being an inhibitor of PI3K-kinase, and component B being suitable pharmaceutically acceptable salt of the alkaline-earth radionuclide radium-223.

In accordance with a third aspect, (claim 3) the present invention comprises combinations of at least two components A and B, component A being an inhibitor of PI3K- kinase or a physiologically acceptable salt thereof, and component B being a suitable pharmaceutically acceptable anorganic salt of the alkaline-earth radionuclide radium-223.

The combinations comprising at least two components A and B, as described and defined herein, are also referred to as "combinations of the present invention".

Further, the present invention relates to:

a kit comprising:
a combination of:
Component A: one or more PI3K-kinase inhibitors as described supra and infra, or a physiologically acceptable salt, solvate, hydrate or stereoisomer thereof;
Component B: a suitable pharmaceutically acceptable salt of the alkaline-earth radionuclide radium-223 or a solvate or a hydrate thereof; and, optionally,
Component C: one or more further pharmaceutical agents;
in which optionally either or both of said components A and B in any of the above-mentioned combinations are in the form of a pharmaceutical formulation/composition which is ready for use to be administered simultaneously, concurrently, separately or sequentially. The components may be administered independently of one another by the oral, intravenous, topical, local installations, intraperitoneal or nasal route.

In accordance with another aspect, the present invention covers the combinations as described supra for the treatment or prophylaxis of a disease.

In accordance with another aspect, the present invention covers the use of such combinations as described supra for the preparation of a medicament for the treatment or prophylaxis of a disease.

DETAILED DESCRIPTION OF THE INVENTION

Definitions

The terms as mentioned in the present text have preferably the following meanings:

The term 'alkyl' refers to a straight or branched hydrocarbon chain radical consisting solely of carbon and hydrogen atoms, containing solely of carbon and hydrogen atoms, containing no unsaturation, having from one to eight carbon atoms, and which is attached to the rest of the molecule by a single bond, such as illustratively, methyl, ethyl, n-propyl 1-methylethyl (isopropyl), n-butyl, n-pentyl, and 1,1-dimethylethyl (t-butyl).

The term "alkenyl" refers to an aliphatic hydrocarbon group containing a carbon-carbon double bond and which may be a straight or branched or branched chain having about 2 to about 10 carbon atoms, e.g., ethenyl, 1-propenyl, 2-propenyl (allyl), iso-propenyl, 2-methyl-1-propenyl, 1-butenyl, 2- and butenyl.

The term "alkynyl" refers to a straight or branched chain hydrocarbonyl radicals having at least one carbon-carbon triple bond, and having in the range of about 2 up to 12 carbon atoms (with radicals having in the range of about 2 up to 10 carbon atoms presently being preferred) e.g., ethynyl.

The term "alkoxy" denotes an alkyl group as defined herein attached via oxygen linkage to the rest of the molecule. Representative examples of those groups are methoxy and ethoxy.

The term "alkoxyakyl" denotes an alkoxy group as defined herein attached via oxygen linkage to an alkyl group which is then attached to the main structure at any carbon from alkyl group that results in the creation of a stable structure the rest of the molecule. Representative examples of those groups are —$CH_2OCH_3$, —$CH_2OC_2H_5$.

The term "cycloalkyl" denotes a non-aromatic mono or multicyclic ring system of about 3 to 12 carbon atoms such as cyclopropyl, cyclobutyl, cyclopentyl, cyclohexyl and examples of multicyclic cycloalkyl groups include perhydronapththyl, adamantyl and norbornyl groups bridged cyclic group or sprirobicyclic groups e.g sprio (4,4) non-2-yl.

The term "cycloalkylalkyl" refers to cyclic ring-containing radicals containing in the range of about about 3 up to 8 carbon atoms directly attached to alkyl group which is then also attached to the main structure at any carbon from the alkyl group that results in the creation of a stable structure such as cyclopropylmethyl, cyclobuyylethyl, cyclopentylethyl.

The term "aryl" refers to aromatic radicals having in the range of 6 up to 14 carbon atoms such as phenyl, naphthyl, tetrahydronapthyl, indanyl, biphenyl.

The term "arylalkyl" refers to an aryl group as defined herein directly bonded to an alkyl group as defined herein which is then attached to the main structure at any carbon from alkyl group that results in the creation of a stable structure the rest of the molecule. e.g., —$CH_2C_6H_5$, —$C_2H_5C_6H_5$.

The term "heterocyclic ring" refers to a stable 3- to 15 membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl cinnolinyl dioxolanyl, indolizinyl, naphthyridinyl, perhydroazepinyl, phenazinyl, phenothiazinyl, phenoxazinyl, phthalazil, pyridyl, pteridinyl, purinyl, quinazolinyl, quinoxalinyl, quinolinyl, isoquinolinyl, tetrazoyl, imidazolyl tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl pyridazinyl, oxazolyl oxazolinyl oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, isochromanyl.

The term "heteroaryl" refers to heterocyclic ring radical as defined herein which are aromatic. The heteroaryl ring radical may be attached to the main structure at any heteroatom or carbon atom that results in the creation of a stable structure.

The heterocyclic ring radical may be attached to the main structure at any heteroatom or carbon atom that results in the creation of a stable structure.

The term "heteroarylalkyl" refers to heteroaryl ring radical as defined herein directly bonded to alkyl group. The heteroarylalkyl radical may be attached to the main structure at any carbon atom from alkyl group that results in the creation of a stable structure.

The term "heterocyclyl" refers to a heterocylic ring radical as defined herein. The heterocylyl ring radical may be attached to the main structure at any heteroatom or carbon atom that results in the creation of a stable structure.

The term "heterocyclylalkyl" refers to a heterocylic ring radical as defined herein directly bonded to alkyl group. The heterocyclylalkyl radical may be attached to the main structure at carbon atom in the alkyl group that results in the creation of a stable structure.

The term "carbonyl" refers to an oxygen atom bound to a carbon atom of the molecule by a double bond.

stituents on a ring may also be present in either cis or trans form. It is intended that all such configurations (including enantiomers and diastereomers), are included within the scope of the present invention. Preferred compounds are those, which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

Tautomers, sometimes referred to as proton-shift tautomers, are two or more compounds that are related by the migration of a hydrogen atom accompanied by the switch of one or more single bonds and one or more adjacent double bonds. The compounds of this invention may exist in one or more tautomeric forms. For example, a compound of Formula I may exist in tautomeric form Ia, tautomeric form Ib, or tautomeric form Ic, or may exist as a mixture of any of these forms. It is intended that all such tautomeric forms are included within the scope of the present invention.

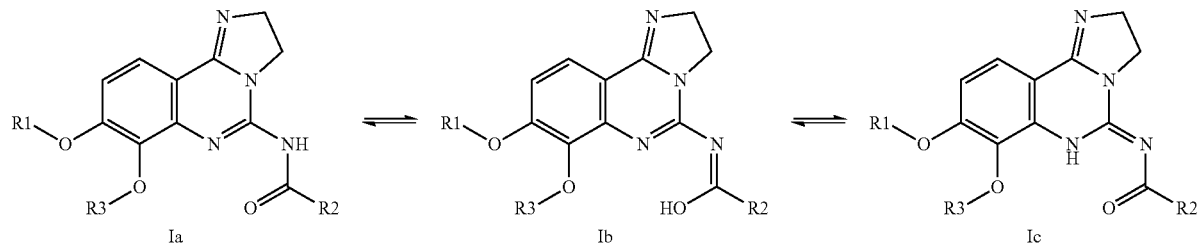

The term "halogen" refers to radicals of fluorine, chlorine, bromine and iodine.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more times", e.g. in the definition of the substituents of the compounds of the present invention (e.g. component A, B or C), is understood as meaning "one, two, three, four or five times, particularly one, two, three or four times, more particularly one, two or three times, even more particularly one or two times".

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The term "carbonyl" refers to an oxygen atom bound to a carbon atom of the molecule by a double bond.

The compounds of this invention may contain one or more asymmetric centers, depending upon the location and nature of the various substituents desired. Asymmetric carbon atoms may be present in the (R)- and/or (S)-configuration, resulting in racemic mixtures in the case of a single asymmetric center, and diastereomeric mixtures in the case of multiple asymmetric centers. In certain instances, asymmetry may also be present due to restricted rotation about a given bond, for example, the central bond adjoining two substituted aromatic rings of the specified compounds. Sub- The present invention also relates to useful forms of the compounds as disclosed herein, such as pharmaceutically acceptable salts, co-precipitates, metabolites, hydrates, solvates and prodrugs of all the compounds of examples. The term "pharmaceutically acceptable salt" refers to a relatively non-toxic, inorganic or organic acid addition salt of a compound of the present invention. For example, see S. M. Berge, et al. "Pharmaceutical Salts," *J. Pharm. Sci.* 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and chorine salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

Representative salts of the compounds of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, chloride, bromide, iodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, sulfate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, or butyl chlorides, bromides and iodides; dialkyl sulfates like dimethyl, diethyl, dibutyl sulfate, or diamyl sulfates, long chain halides such as decyl, lauryl, myristyl and strearyl chlorides, bromides and iodides, aralkyl halides like benzyl and phenethyl bromides and others.

A solvate for the purpose of this invention is a complex of a solvent and a compound of the invention in the solid state. Exemplary solvates would include, but are not limited to, complexes of a compound of the invention with ethanol or methanol. Hydrates are a specific form of solvate wherein the solvent is water.

Constituents which are optionally substituted as stated herein, may be substituted, unless otherwise noted, one or more times, independently from one another at any possible position. When any variable occurs more than one time in any constituent, each definition is independent.

The heteroarylic, or heterocyclic groups mentioned herein can be substituted by their given substituents or parent molecular groups, unless otherwise noted, at any possible position, such as e.g. at any substitutable ring carbon or ring nitrogen atom. Analogously it is being understood that it is possible for any heteroaryl or heterocyclyl group to be attached to the rest of the molecule via any suitable atom if chemically suitable. Unless otherwise noted, any heteroatom of a heteroarylic ring with unsatisfied valences mentioned herein is assumed to have the hydrogen atom(s) to satisfy the valences. Unless otherwise noted, rings containing quaternizable amino- or imino-type ring nitrogen atoms (—N=) may be preferably not quaternized on these amino- or imino-type ring nitrogen atoms by the mentioned substituents or parent molecular groups.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques already known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Diacel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

If in the context of the invention "embodiment" is mentioned it should be understood to include a plurality of possible combinations.

In order to limit different types of isomers from each other reference is made to IUPAC Rules Section E (Pure Appl Chem 45, 11-30, 1976).

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature.

Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

The present invention includes all possible stereoisomers of the compounds of the present invention as single stereoisomers, or as any mixture of said stereoisomers, in any ratio. Isolation of a single stereoisomer, e.g. a single enantiomer or a single diastereomer, of a compound of the present invention may be achieved by any suitable state of the art method, such as chromatography, especially chiral chromatography, for example.

The present invention includes all possible tautomers of the compounds of the present invention as single tautomers, or as any mixture of said tautomers, in any ratio.

Furthermore, the present invention includes all possible crystalline forms, or polymorphs, of the compounds of the present invention, either as single polymorphs, or as a mixture of more than one polymorphs, in any ratio.

Component A of the Combination

Component A can be selected from inhibitors of PI3K-kinase specifically or generically disclosed e.g. in the publications as mentioned above which are incorporated herein by reference.

In an embodiment, said component A is a compound of general formula (A):

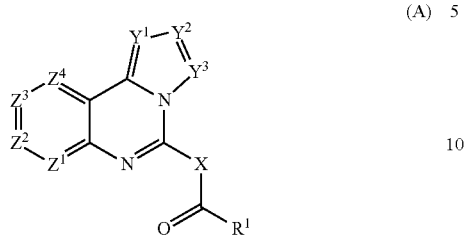

(A)

in which:
X represents $CR^5R^6$ or NH;
$Y^1$ represents $CR^3$ or N;
the chemical bond between $Y^2=Y^3$ represents a single bond or double bond,
with the proviso that when the $Y^2=Y^3$ represents a double bond, $Y^2$ and $Y^3$ independently represent $CR^4$ or N, and when $Y^2=Y^3$ represents a single bond, $Y^2$ and $Y^3$ independently represent $CR^3R^4$ or $NR^4$;
$Z^1$, $Z^2$, $Z^3$ and $Z^4$ independently represent CH, $CR^2$ or N;
$R^1$ represents aryl optionally having 1 to 3 substituents selected from $R^{11}$, $C_{3-8}$ cycloalkyl optionally having 1 to 3 substituents selected from $R^{11}$, $C_{1-6}$ alkyl optionally substituted by aryl, heteroaryl, $C_{1-6}$ alkoxyaryl, aryloxy, heteroaryloxy or one or more halogen,
$C_{1-6}$ alkoxy optionally substituted by carboxy, aryl, heteroaryl, $C_{1-6}$ alkoxyaryl, aryloxy, heteroaryloxy or one or more halogen,
or
a 3 to 15 membered mono- or bi-cyclic heterocyclic ring that is saturated or unsaturated, optionally having 1 to 3 substituents selected from $R^{11}$, and contains 1 to 3 heteroatoms selected from the group consisting of N, O and S,
wherein
$R^{11}$ represents halogen, nitro, hydroxy, cyano, carboxy, amino, N—($C_{1-6}$ alkyl)amino, N-(hydroxy$C_{1-6}$ alkyl)amino, N,N-di($C_{1-6}$ alkyl)amino, N—($C_{1-6}$ acyl)amino, N-(formyl)-N—($C_{1-6}$ alkyl)amino, N—($C_{1-6}$ alkanesulfonyl) amino, N-(carboxy$C_{1-6}$ alkyl)-N—($C_{1-6}$ alkyl)amino, N—($C_{1-6}$alkoxycabonyl)amino, N—[N,N-di($C_{1-6}$ alkyl)amino methylene]amino, N—[N,N-di($C_{1-6}$ alkyl)amino ($C_{1-6}$ alkyl)methylene]amino, N—[N,N-di($C_{1-6}$alkyl)amino $C_{2-6}$ alkenyl]amino, aminocarbonyl, N—($C_{1-6}$ alkyl)aminocarbonyl, N,N-di($C_{1-6}$ alkyl)aminocarbonyl, $C_{3-8}$ cycloalkyl, $C_{1-6}$ alkylthio, $C_{1-6}$ alkanesulfonyl, sulfamoyl, $C_{1-6}$ alkoxycarbonyl, N-arylamino wherein said aryl moiety is optionally having 1 to 3 substituents selected from $R^{101}$, N-(aryl $C_{1-6}$ alkyl)amino wherein said aryl moiety is optionally having 1 to 3 substituents selected from $R^{101}$, aryl $C_{1-6}$ alkoxycarbonyl wherein said aryl moiety is optionally having 1 to 3 substituents selected from $R^{101}$,
$C_{1-6}$ alkyl optionally substituted by mono-, di- or tri-halogen, amino, N—($C_{1-6}$ alkyl)amino or N,N-di($C_{1-6}$ alkyl)amino,
$C_{1-6}$ alkoxy optionally substituted by mono-, di- or tri-halogen, N—($C_{1-6}$ alkyl)sulfonamide, or N-(aryl) sulfonamide,
or
a 5 to 7 membered saturated or unsaturated ring having 1 to 3 heteroatoms selected from the group consisting of O, S and N, and optionally having 1 to 3 substituents selected from $R^{101}$
wherein
$R^{101}$ represents halogen, carboxy, amino, N—($C_{1-6}$ alkyl)amino, N,N-di($C_{1-6}$alkyl)amino, aminocarbonyl, N—($C_{1-6}$ alkyl)aminocarbonyl, N,N-di($C_{1-6}$ alkyl)aminocarbonyl, pyridyl,
$C_{1-6}$ alkyl optionally substituted by cyano or mono- di- or tri-halogen,
and
$C_{1-6}$ alkoxy optionally substituted by cyano, carboxy, amino, N—($C_{1-6}$ alkyl)amino, N,N-di($C_{1-6}$ alkyl)amino, aminocarbonyl, N—($C_{1-6}$alkyl) aminocarbonyl, N,N-di($C_{1-6}$ alkyl)aminocarbonyl or mono-, di- or tri-halogen;
$R^2$ represents hydroxy, halogen, nitro, cyano, amino, N—($C_{1-6}$ alkyl)amino, N,N-di($C_{1-6}$ alkyl)amino, N-(hydroxy$C_{1-6}$ alkyl)amino, N-(hydroxy$C_{1-6}$ alkyl)-N—($C_{1-6}$ alkyl)amino, $C_{1-6}$ acyloxy, amino$C_{1-6}$ acyloxy, $C_{2-6}$ alkenyl, aryl,
a 5-7 membered saturated or unsaturated heterocyclic ring having 1 to 3 heteroatoms selected from the group consisting O, S and N, and optionally substituted by
hydroxy, $C_{1-6}$ alkyl, $C_{1-6}$ alkoxy, oxo, amino, amino $C_{1-6}$ alkyl, N—($C_{1-6}$ alkyl)amino, N,N-di($C_{1-6}$ alkyl) amino, N—($C_{1-6}$ acyl)amino, N—($C_{1-6}$ alkyl)carbonylamino, phenyl, phenyl $C_{1-6}$ alkyl, carboxy, $C_{1-6}$ alkoxycarbonyl, aminocarbonyl, N—($C_{1-6}$ alkyl)aminocarbonyl, or N,N-di($C_{1-6}$ alkyl)amino, —C(O)— $R^{20}$
wherein
$R^{20}$ represents $C_{1-6}$ alkyl, $C_{1-6}$ alkoxy, amino, N—($C_{1-6}$alkyl)amino, N,N-di($C_{1-6}$ alkyl)amino, N—($C_{1-6}$ acyl)amino, or a 5-7 membered saturated or unsaturated heterocyclic ring having 1 to 3 heteroatoms selected from the group consisting O, S and N, and optionally substituted by $C_{1-6}$ alkyl, $C_{1-6}$ alkoxy, oxo, amino, N—($C_{1-6}$alkyl)amino, N,N-di($C_{1-6}$ alkyl)amino, N—($C_{1-6}$ acyl)amino, phenyl, or benzyl,
$C_{1-6}$ alkyl optionally substituted by $R^{21}$,
or
$C_{1-6}$ alkoxy optionally substituted by $R^{21}$,
wherein
$R^{21}$ represents cyano, mono-, di or tri-halogen, amino, N—($C_{1-6}$alkyl)amino, N,N-di($C_{1-6}$ alkyl) amino, N-(hydroxy$C_{1-6}$ alkyl) amino, N-(halophenyl$C_{1-6}$ alkyl) amino, amino $C_{2-6}$ alkylenyl, $C_{1-6}$ alkoxy, hydroxy$C_{1-6}$ alkoxy, —C(O)—$R^{201}$, —NHC(O)—$R^{201}$, $C_{3-8}$ cycloalkyl, isoindolino, phthalimidyl, 2-oxo-1,3-oxazolidinyl, aryl or a 5 or 6 membered saturated or unsaturated heterocyclic ring having 1 to 4 heteroatoms selected from the group consisting 0, S and N, and optionally substituted by hydroxy, $C_{1-6}$ alkyl, $C_{1-6}$ alkoxy, $C_{1-6}$ alkoxycarbonyl, hydroxy$C_{1-6}$ alkoxy, oxo, amino, amino$C_{1-6}$ alkyl, N—($C_{1-6}$ alkyl)amino, N,N-di($C_{1-6}$ alkyl)amino, N—($C_{1-6}$ acyl)amino, or benzyl,
wherein
$R^{201}$ represents hydroxy, amino, N—($C_{1-6}$ alkyl) amino, N,N-di($C_{1-6}$ alkyl)amino, N-(halophenyl$C_{1-6}$ alkyl) amino, $C_{1-6}$ alkyl, amino$C_{1-6}$ alkyl, amino$C_{2-6}$ alkylenyl, $C_{1-6}$ alkoxy, a 5 or 6 membered saturated or unsaturated heterocyclic ring having 1 to 4 heteroatoms selected from the group consisting O, S and N, and optionally substituted by hydroxy, $C_{1-6}$ alkyl, $C_{1-6}$ alkoxy, $C_{1-6}$ alkoxycarbonyl, hydroxy$C_{1-6}$ alkoxy, oxo, amino, N—($C_{1-6}$ alkyl)amino, N,N-di($C_{1-6}$ alkyl)amino, N—($C_{1-6}$ acyl)amino or benzyl;

$R^3$ represents hydrogen, halogen, aminocarbonyl, or $C_{1-6}$ alkyl optionally substituted by aryl $C_{1-6}$ alkoxy or mono-, di- or tri-halogen;

$R^4$ represents hydrogen or $C_{1-6}$ alkyl;

$R^5$ represents hydrogen or $C_{1-6}$ alkyl; and $R^6$ represents halogen, hydrogen or $C_{1-6}$ alkyl, or a physiologically acceptable salt, solvate, hydrate or stereoisomer thereof.

In an embodiment, said component A is a compound of general formula (A), supra, which is selected from the list consisting of:

N-(7,8-dimethoxy-2,3-dihydroimidazo[1,2-c]quinazolin-5-yl)nicotinamide;
2-(7, 8-dimethoxy-2,3-dihydroimidazo[1,2-c]quinazolin-5-yl)-1-pyridin-3-ylethylenol;
N-(7, 8-dimethoxy-2,3-dihydroimidazo[1,2-c]quinazolin-5-yl)-1H-benzimidazole-5-carboxamide;
6-(acetamido)-N-(7,8-dimethoxy-2,3-dihydroimidazo[1,2-c]quinazolin-5-yl)nicotinamide;
N-{5-[2-(7,8-dimethoxy-2,3-dihydroimidazo[1,2-c]quinazolin-5-yl)-1-hydroxyvinyl]pyridin-2-yl}acetamide;
2-({5-[2-hydroxy-2-pyridin-3-ylvinyl]-7-methoxy-2,3-dihydroimidazo[1,2-c]quinazolin-8-yl}oxy)-N,N-dimethylacetamide;
2-[7-methoxy-8-(tetrahydro-2H-pyran-2-ylmethoxy)-2,3-dihydroimidazo[1,2-c]quinazolin-5-yl]-1-pyridin-3-ylethylenol;
2-[8-(2-hydroxyethoxy)-7-methoxy-2,3-dihydroimidazo[1,2-c]quinazolin-5-yl]-1-pyridin-3-ylethylenol;
({5-[2-hydroxy-2-pyridin-3-ylvinyl]-7-methoxy-2,3-dihydroimidazo[1,2-c]quinazolin-8-yl}oxy)acetic acid;
4-({5-[2-hydroxy-2-pyridin-3-ylvinyl]-7-methoxy-2,3-dihydroimidazo[1,2-c]quinazolin-8-yl}oxy)butanoic acid;
({5-[2-hydroxy-2-pyridin-3-ylvinyl]-7-methoxy-2,3-dihydroimidazo[1,2-c]quinazolin-8-yl}oxy)acetonitrile;
2-[7-methoxy-8-(2H-tetrazol-5-ylmethoxy)-2,3-dihydroimidazo[1,2-c]quinazolin-5-yl]-1-pyridin-3-ylethylenol;
2-[7-methoxy-8-(4-morpholin-4-yl-4-oxobutoxy)-2,3-dihydroimidazo[1,2-c]quinazolin-5-yl]-1-pyridin-3-ylethylenol;
5-[1-hydroxy-2-(8-morpholin-4-yl-2,3-dihydroimidazo[1,2-c]quinazolin-5-yl)vinyl]pyridin-3-ol;
N-(2,3-dihydroimidazo[1,2-c]quinazolin-5-yl)-5-hydroxynicotinamide;
6-(acetamido)-N-(7,9-dimethoxy-8-methyl-2,3-dihydroimidazo[1,2-c]quinazolin-5-yl)nicotinamide;
N-(8,9-dimethoxy-2,3-dihydroimidazo[1,2-c]quinazolin-5-yl)-5-hydroxynicotinamide; 5-hydroxy-N-(7-methoxy-2,3-dihydroimidazo[1,2-c]quinazolin-5-yl)nicotinamide;
N-(7,8-dimethoxy-2,3-dihydroimidazo[1,2-c]quinazolin-5-yl)-5-[(4-methoxybenzyl)oxy]nicotinamide;
N-(7,8-dimethoxy-2,3-dihydroimidazo[1,2-c]quinazolin-5-yl)-5-hydroxynicotinamide;
5-hydroxy-N-[8-(trifluoromethyl)-2,3-dihydroimidazo[1,2-c]quinazolin-5-yl]nicotinamide;
N-{8-[3-(1,3-dioxo-1,3-dihydro-2H-isoindol-2-yl)propoxy]-2,3-dihydroimidazo[1,2-c]quinazolin-5-yl}nicotinamide;
N-(7-bromo-8-methoxy-2,3-dihydroimidazo[1,2-c]quinazolin-5-yl)nicotinamide;
6-amino-N-(8-methoxy-2,3-dihydroimidazo[1,2-c]quinazolin-5-yl)nicotinamide;
1-(1H-benzimidazol-5-yl)-2-(8,9-dimethoxy-2,3-dihydroimidazo[1,2-c]quinazolin-5-yl)ethylenol;
2-(8,9-dimethoxy-2,3-dihydroimidazo[1,2-c]quinazolin-5-yl)-1-(2,4-dimethyl-1,3-thiazol-5-yl)ethylenol;
N-(9-methoxy-2,3-dihydroimidazo[1,2-c]quinazolin-5-yl)-1H-benzimidazole-5-carboxamide;
N-(8-bromo-2,3-dihydroimidazo[1,2-c]quinazolin-5-yl)nicotinamide;
N-(8-bromo-2,3-dihydroimidazo[1,2-c]quinazolin-5-yl)-1H-benzimidazole-5-carboxamide;
N-(8-methoxy-2,3-dihydroimidazo[1,2-c]quinazolin-5-yl)-1H-benzimidazole-5-carboxamide;
N-(8-methyl-2,3-dihydroimidazo[1,2-c]quinazolin-5-yl)-1H-benzimidazole-5-carboxamide;
N-[8-(trifluoromethyl)-2,3-dihydroimidazo[1,2-c]quinazolin-5-yl]-1H-benzimidazole-5-carboxamide;
N-(7-fluoro-2,3-dihydroimidazo[1,2-c]quinazolin-5-yl)-1H-benzimidazole-5-carboxamide;
N-(7-methoxy-2,3-dihydroimidazo[1,2-c]quinazolin-5-yl)nicotinamide;
N-(8-chloro-2,3-dihydroimidazo[1,2-c]quinazolin-5-yl)-1H-benzimidazole-5-carboxamide;
6-(acetamido)-N-(8-morpholin-4-yl-2,3-dihydroimidazo[1,2-c]quinazolin-5-yl)nicotinamide;
1-(1H-benzimidazol-5-yl)-2-(8-morpholin-4-yl-2,3-dihydroimidazo[1,2-c]quinazolin-5-yl)ethylenol;
N-{5-[1-hydroxy-2-(8-morpholin-4-yl-2,3-dihydroimidazo[1,2-c]quinazolin-5-yl)vinyl]pyridin-2-yl}acetamide;
6-methyl-N-(8-morpholin-4-yl-2,3-dihydroimidazo[1,2-c]quinazolin-5-yl)nicotinamide;
1-(1H-benzimidazol-5-yl)-2-[8-(4-methylpiperazin-1-yl)-2,3-dihydroimidazo[1,2-c]quinazolin-5-yl]ethylenol;
N-(2,3-dihydroimidazo[1,2-c]quinazolin-5-yl)-3H-imidazo[4,5-b]pyridine-6-carboxamide;
N-(7,8-dimethoxy-2,3-dihydroimidazo[1,2-c]quinazolin-5-yl)-3H-imidazo[4,5-b]pyridine-6-carboxamide;
N-[7-(trifluoromethyl)-2,3-dihydroimidazo[1,2-c]quinazolin-5-yl]-1H-benzimidazole-5-carboxamide;
N-(7,9-dimethoxy-2,3-dihydroimidazo[1,2-c]quinazolin-5-yl)-1H-benzimidazole-5-carboxamide;
N-{5-[2-(7,9-dimethoxy-8-methyl-2,3-dihydroimidazo[1,2-c]quinazolin-5-yl)-1-hydroxyvinyl]pyridin-2-yl}acetamide;
N-{5-[2-(7-bromo-9-methyl-2,3-dihydroimidazo[1,2-c]quinazolin-5-yl)-1-hydroxyvinyl]pyridin-2-yl}acetamide; and
2-(8,9-dimethoxy-2,3-dihydroimidazo[1,2-c]quinazolin-5-yl)-1-pyridin-3-ylethylenol;

In an embodiment, said component A is a compound having the formula (I):

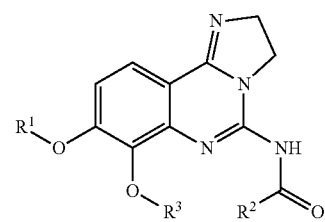

or a physiologically acceptable salt, solvate, hydrate or stereoisomer thereof, in which:

$R^1$ represents —$(CH_2)_n$—$(CHR^4)$—$(CH_2)_m$—$N(R^5)(R^{5'})$;

$R^2$ represents a heteroaryl optionally substituted with 1, 2 or 3 $R^6$ groups;

$R^3$ represents alkyl or cycloalkyl;

$R^4$ represents hydrogen or alkoxy; and $R^5$ and $R^{5'}$ may be the same or different and represent independently, hydrogen, alkyl, cycloalkylalklyl, or alkoxyalkyl or $R^5$ and $R^{5'}$ may be taken together with the nitrogen atom to which they are bound to form a 3-7 membered nitrogen containing heterocyclic ring optionally containing at least one additional heteroatom selected from oxygen, nitrogen or sulfur and which may be optionally substituted with 1 or more $R^{6'}$ groups, or $R^4$ and $R^5$ may be taken together with the atoms to which they are bound to form a 5-6 membered nitrogen containing heterocyclic ring optionally containing 1 or more nitrogen, oxygen or sulfur atoms and which may be optionally substituted with 1 or more $R^{6'}$ groups;

each occurrence of $R^6$ may be the same or different and is independently halogen, alkyl, alkenyl, alkynyl, cycloalkyl, cycloalkylalklyl, aryl, arylalkyl, heteroaryl, heteroarylalkyl, heterocyclic ring, heterocyclylalkyl, alkyl-$OR^7$, alkyl-$SR^7$, alkyl-$N(R^7)(R^{7'})$, alkyl-$COR^7$, —CN, —$COOR^7$, —$CON(R^7)(R^{7'})$, —$OR^7$, —$SR^7$, —$N(R^7)(R^{7'})$, or —$NR^7COR^7$ each of which may be optionally substituted with 1 or more $R^8$ groups;

each occurrence of $R^{6'}$ may be the same or different and is independently alkyl, cycloalkylalklyl, or alkyl-$OR^7$;

each occurrence of $R^7$ and $R^{7'}$ may be the same or different and is independently hydrogen, alkyl, alkenyl, alkynyl, cycloalkyl, cycloalkylalklyl, cycloalkenyl, aryl, arylalkyl, heteroaryl, heterocyclic ring, heterocyclylalkyl, or heteroarylalkyl;

each occurrence of $R^8$ is independently nitro, hydroxy, cyano, formyl, acetyl, halogen, amino, alkyl, alkoxy, alkenyl, alkynyl, cycloalkyl, cycloalkylalklyl, cycloalkenyl, aryl, arylalkyl, heteroaryl, heterocyclic ring, heterocyclylalkyl, or heteroarylalkyl;

n is an integer from 1-4 and m is an integer from 0-4 with the proviso that when when $R^4$ and $R^5$ are taken together with the atoms to which they are bound to form a 5-6 membered nitrogen containing ring, n+m≤4;

or a physiologically acceptable salt, solvate, hydrate or stereoisomer thereof.

In an embodiment, said component A is a compound having the formula (I), supra, in which $R^2$ is a nitrogen containing heteroaryl optionally substituted with 1, 2 or 3 $R^6$ groups, or a physiologically acceptable salt, solvate, hydrate or stereoisomer thereof.

In an embodiment, said component A is a compound of general formula (I), supra, in which $R^5$ and $R^{5'}$ are independently alkyl, or a physiologically acceptable salt, solvate, hydrate or stereoisomer thereof.

In an embodiment, said component A is a compound of general formula (I), supra, in which $R^5$ and $R^{5'}$ are taken together with the nitrogen atom to which they are bound to form a 5-6 membered nitrogen containing heterocyclic ring containing at least one additional heteroatom selected from oxygen, nitrogen or sulfur and which may be optionally substituted with 1 or more $R^{6'}$ groups, or a physiologically acceptable salt, solvate, hydrate or stereoisomer thereof.

In an embodiment, said component A is a compound of formula (I) in which $R^4$ and $R^5$ are taken together with the atoms to which they are bound to form a 5-6 membered nitrogen containing heterocyclic ring optionally containing 1 or more nitrogen, oxygen or sulfur atoms and which may be optionally substituted with 1 or more $R^6$ groups, or a physiologically acceptable salt, solvate, hydrate or stereoisomer thereof.

In an embodiment, said component A is a compound of formula (I) in which $R^3$ is methyl,
or a physiologically acceptable salt, solvate, hydrate or stereoisomer thereof.

In an embodiment, said component A is a compound of formula (I), wherein $R^2$ is pyridine, pyridazine, pyrimidine, pyrazine, pyrole, oxazole, thiazole, furan or thiophene, optionally substituted with 1, 2 or 3 $R^6$ groups; more preferably pyridine, pyridazine, pyrimidine, pyrazine, pyrole, oxazole or thiazole, optionally substituted with 1, 2 or 3 $R^6$ groups,
or a physiologically acceptable salt, solvate, hydrate or stereoisomer thereof.

In an embodiment, said component A is a compound of formula (Ia):

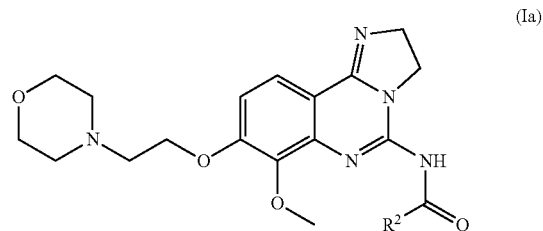

(Ia)

or a physiologically acceptable salt, solvate, hydrate or stereoisomer thereof, wherein $R^2$ is as defined above for formula (I).

In an embodiment, said component A is a compound of formula (Ib):

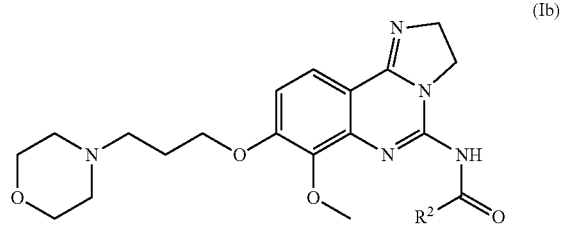

(Ib)

or a physiologically acceptable salt, solvate, hydrate or stereoisomer thereof, wherein $R^2$ is as defined above for formula (I).

In an embodiment, said component A is a compound of formula (Ic):

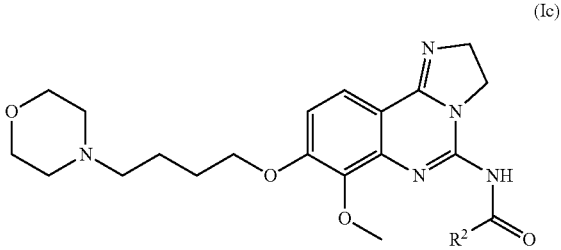

(Ic)

or a physiologically acceptable salt, solvate, hydrate or stereoisomer thereof, wherein $R^2$ is as defined above for formula (I).

In an embodiment, said component A is a compound of the formula (Id):

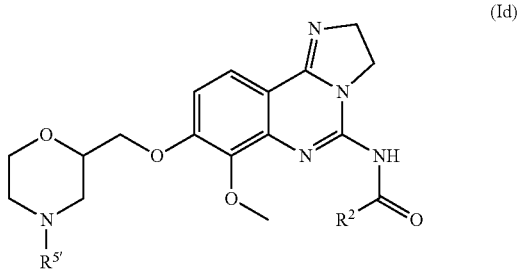

(Id)

or a physiologically acceptable salt, solvate, hydrate or stereoisomer thereof, wherein $R^2$ and $R^4$ are as defined above for formula (I).

In an embodiment, said component A is a compound of the formula (Ie):

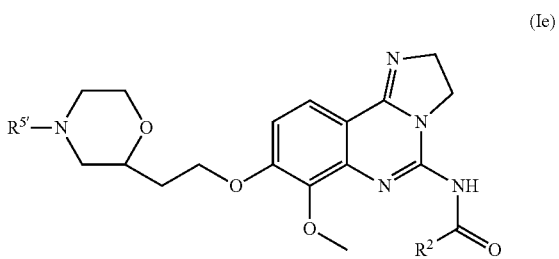

(Ie)

or a physiologically acceptable salt, solvate, hydrate or stereoisomer thereof, wherein $R^2$ and $R^4$ are as defined above for formula (I).

In an embodiment, said component A is a compound of formula (I)-(Ie), wherein $R^2$ is pyridine, pyridazine, pyrimidine, pyrazine, pyrole, oxazole, thiazole, furan or thiophene, optionally substituted with 1, 2 or 3 $R^6$ groups; more preferrably wherein $R^2$ is pyridine, pyridazine, pyrimidine, pyrazine, pyrole, oxazole or thiazole, optionally substituted with 1, 2 or 3 $R^6$ groups, or a physiologically acceptable salt, solvate, hydrate or stereoisomer thereof.

In an embodiment, said component A is a compound selected from the list consisting of:

N-[7-methoxy-8-(3-morpholin-4-ylpropoxy)-2,3-dihydroimidazo[1,2-c]quinazolin-5-yl]pyrimidine-5-carboxamide;

N-(8-{3-[(2R,6S)-2,6-dimethylmorpholin-4-yl]propoxy}-7-methoxy-2,3-dihydroimidazo[1,2-c]quinazolin-5-yl)nicotinamide;

N-(8-{3-[(2R,6S)-2,6-dimethylmorpholin-4-yl]propoxy}-7-methoxy-2,3-dihydroimidazo[1,2-c]quinazolin-5-yl)-2,4-dimethyl-1,3-thiazole-5-carboxamide;

2-amino-N-[7-methoxy-8-(3-morpholin-4-ylpropoxy)-2,3-dihydroimidazo[1,2-c]quinazolin-5-yl]-1,3-thiazole-5-carboxamide;

2-amino-N-[7-methoxy-8-(3-morpholin-4-ylpropoxy)-2,3-dihydroimidazo[1,2-c]quinazolin-5-yl]isonicotinamide;

2-amino-N-[7-methoxy-8-(3-morpholin-4-ylpropoxy)-2,3-dihydroimidazo[1,2-c]quinazolin-5-yl]-4-methyl-1,3-thiazole-5-carboxamide;

2-amino-N-[7-methoxy-8-(3-morpholin-4-ylpropoxy)-2,3-dihydroimidazo[1,2-c]quinazolin-5-yl]-4-propylpyrimidine-5-carboxamide;

N-{8-[2-(4-ethylmorpholin-2-yl)ethoxy]-7-methoxy-2,3-dihydroimidazo[1,2-c]quinazolin-5-yl}nicotinamide;

N-{8-[2-(dimethylamino)ethoxy]-7-methoxy-2,3-dihydroimidazo[1,2-c]quinazolin-5-yl}pyrimidine-5-carboxamide;

N-(8-{3-[2-(hydroxymethyl) morpholin-4-yl]propoxy}-7-methoxy-2,3-dihydroimidazo[1,2-c]quinazolin-5-yl)nicotinamide;

N-(8-{3-[2-(hydroxymethyl) morpholin-4-yl]propoxy}-7-methoxy-2,3-dihydroimidazo[1,2-c]quinazolin-5-yl)nicotinamide;

N-{8-[3-(dimethylamino)propoxy]-7-methoxy-2,3-dihydroimidazo[1,2-c]quinazolin-5-yl}nicotinamide 1-oxide;

2-amino-N-[7-methoxy-8-(3-morpholin-4-ylpropoxy)-2,3-dihydroimidazo[1,2-c]quinazolin-5-yl]pyrimidine-5-carboxamide;

N-[7-methoxy-8-(3-morpholin-4-ylpropoxy)-2,3-dihydroimidazo[1,2-c]quinazolin-5-yl]-6-(2-pyrrolidin-1-ylethyl)nicotinamide;

6-(cyclopentylamino)-N-[7-methoxy-8-(3-morpholin-4-ylpropoxy)-2,3-dihydroimidazo[1,2-c]quinazolin-5-yl] nicotinamide;

N-[8-(2-hydroxy-3-morpholin-4-ylpropoxy)-7-methoxy-2,3-dihydroimidazo[1,2-c]quinazolin-5-yl]nicotinamide;

N-{7-methoxy-8-[3-(3-methylmorpholin-4-yl)propoxy]-2,3-dihydroimidazo[1,2-c]quinazolin-5-yl}nicotinamide;

N-(8-{3-[2-(hydroxymethyl) morpholin-4-yl]propoxy}-7-methoxy-2,3-dihydroimidazo[1,2-c]quinazolin-5-yl)nicotinamide;

N-(8-{2-[4-(cyclobutylmethyl) morpholin-2-yl]ethoxy}-7-methoxy-2,3-dihydroimidazo[1,2-c]quinazolin-5-yl)nicotinamide;

N-(7-methoxy-8-{2-[4-(2-methoxyethyl)morpholin-2-yl]ethoxy}-2,3-dihydroimidazo[1,2-c]quinazolin-5-yl)nicotinamide;

N-{8-[(4-ethylmorpholin-2-yl)methoxy]-7-methoxy-2,3-dihydroimidazo[1,2-c]quinazolin-5-yl}nicotinamide;

N-(7-methoxy-8-{[4-(2-methoxyethyl)morpholin-2-yl]methoxy}-2,3-dihydroimidazo[1,2-c]quinazolin-5-yl) nicotinamide;

N-{7-methoxy-8-[(4-methyl morpholin-2-yl)methoxy]-2,3-dihydroimidazo[1,2-c]quinazolin-5-yl}nicotinamide;

N-[7-methoxy-8-(3-morpholin-4-ylpropoxy)-2,3-dihydroimidazo[1,2-c]quinazolin-5-yl]pyrimidine-4-carboxamide;

2-amino-N-[7-methoxy-8-(3-morpholin-4-ylpropoxy)-2,3-dihydroimidazo[1,2-c]quinazolin-5-yl]pyrimidine-4-carboxamide;

N-[7-methoxy-8-(3-morpholin-4-ylpropoxy)-2,3-dihydroimidazo[1,2-c]quinazolin-5-yl]-1-methyl-1H-imidazole-4-carboxamide;

rel-N-(8-{3-[(2R,6S)-2,6-dimethylmorpholin-4-yl]propoxy}-7-methoxy-2,3-dihydroimidazo[1,2-c]quinazolin-5-yl)pyrimidine-5-carboxamide;

rel-N-(8-{3-[(2R,6S)-2,6-dimethylmorpholin-4-yl]propoxy}-7-methoxy-2,3-dihydroimidazo[1,2-c]quinazolin-5-yl)-6-methylnicotinamide;

rel-6-acetamido-N-(8-{3-[(2R,6S)-2,6-dimethyl morpholin-4-yl]propoxy}-7-methoxy-2,3-dihydroimidazo[1,2-c]quinazolin-5-yl)nicotinamide;

N-[7-methoxy-8-(3-morpholin-4-ylpropoxy)-2,3-dihydroimidazo[1,2-c]quinazolin-5-yl]-1-methyl-1H-imidazole-5-carboxamide;

6-amino-N-[7-methoxy-8-(3-morpholin-4-ylpropoxy)-2,3-dihydroimidazo[1,2-c]quinazolin-5-yl]-2-methylnicotinamide;

2-amino-N-[7-methoxy-8-(3-morpholin-4-ylpropoxy)-2,3-dihydroimidazo[1,2-c]quinazolin-5-yl]-4-methylpyrimidine-5-carboxamide;

6-amino-5-bromo-N-[7-methoxy-8-(3-morpholin-4-ylpropoxy)-2,3-dihydroimidazo[1,2-c]quinazolin-5-yl]nicotinamide;

2-amino-N-[7-methoxy-8-(3-morpholin-4-ylpropoxy)-2,3-dihydroimidazo[1,2-c]quinazolin-5-yl]-1,3-oxazole-5-carboxamide;

N-[7-methoxy-8-(morpholin-2-ylmethoxy)-2,3-dihydroimidazo[1,2-c]quinazolin-5-yl]nicotinamide;

2-{[2-(dimethylamino)ethyl]amino}-N-{8-[3-(dimethylamino)propoxy]-7-methoxy-2,3-dihydroimidazo[1,2-c]quinazolin-5-yl}pyrimidine-5-carboxamide;

2-amino-N-{8-[3-(dimethylamino)propoxy]-7-methoxy-2,3-dihydroimidazo[1,2-c]quinazolin-5-yl}-1,3-thiazole-5-carboxamide;

rel-2-amino-N-(8-{3-[(2R,6S)-2,6-dimethylmorpholin-4-yl]propoxy}-7-methoxy-2,3-dihydroimidazo[1,2-c]quinazolin-5-yl)pyrimidine-5-carboxamide;

rel-6-amino-N-(8-{3-[(2R,6S)-2,6-dimethylmorpholin-4-yl]propoxy}-7-methoxy-2,3-dihydroimidazo[1,2-c]quinazolin-5-yl)nicotinamide;

2-[(2-hydroxyethyl)amino]-N-[7-methoxy-8-(3-morpholin-4-ylpropoxy)-2,3-dihydroimidazo[1,2-c]quinazolin-5-yl]pyrimidine-5-carboxamide;

N-[7-methoxy-8-(3-morpholin-4-ylpropoxy)-2,3-dihydroimidazo[1,2-c]quinazolin-5-yl]-2-[(3-methoxypropyl)amino]pyrimidine-5-carboxamide;

2-amino-N-{8-[3-(dimethylamino)propoxy]-7-methoxy-2,3-dihydroimidazo[1,2-c]quinazolin-5-yl}pyrimidine-5-carboxamide;

N-[7-methoxy-8-(3-morpholin-4-ylpropoxy)-2,3-dihydroimidazo[1,2-c]quinazolin-5-yl]-2-[(3-morpholin-4-ylpropyl)amino]pyrimidine-5-carboxamide;

2-[(2-methoxyethyl)amino]-N-[7-methoxy-8-(3-morpholin-4-ylpropoxy)-2,3-dihydroimidazo[1,2-c]quinazolin-5-yl]pyrimidine-5-carboxamide;

2-{[2-(dimethyl amino)ethyl]amino}-N-[7-methoxy-8-(3-morpholin-4-ylpropoxy)-2,3-dihydroimidazo[1,2-c]quinazolin-5-yl]pyrimidine-5-carboxamide;

6-amino-N-{8-[3-(dimethylamino)propoxy]-7-methoxy-2,3-dihydroimidazo[1,2-c]quinazolin-5-yl}nicotinamide;

N-[7-methoxy-8-(3-morpholin-4-ylpropoxy)-2,3-dihydroimidazo[1,2-c]quinazolin-5-yl]-2-pyrrolidin-1-ylpyrimidine-5-carboxamide;

N-[7-methoxy-8-(3-morpholin-4-ylpropoxy)-2,3-dihydroimidazo[1,2-c]quinazolin-5-yl]-2-(4-methylpiperazin-1-yl)pyrimidine-5-carboxamide;

N-[7-methoxy-8-(3-morpholin-4-ylpropoxy)-2,3-dihydroimidazo[1,2-c]quinazolin-5-yl]-2-morpholin-4-ylpyrimidine-5-carboxamide;

N-[7-methoxy-8-(3-morpholin-4-ylpropoxy)-2,3-dihydroimidazo[1,2-c]quinazolin-5-yl]-6-piperazin-1-ylnicotinamide hydrochloride;

6-[(3S)-3-aminopyrrolidin-1-yl]-N-[7-methoxy-8-(3-morpholin-4-ylpropoxy)-2,3-dihydroimidazo[1,2-c]quinazolin-5-yl]nicotinamide hydrochloride hydrate;

6-[(3R)-3-aminopyrrolidin-1-yl]-N-[7-methoxy-8-(3-morpholin-4-ylpropoxy)-2,3-dihydroimidazo[1,2-c]quinazolin-5-yl]nicotinamide hydrochloride;

6-[(4-fluorobenzyl)amino]-N-[7-methoxy-8-(3-morpholin-4-ylpropoxy)-2,3-dihydroimidazo[1,2-c]quinazolin-5-yl]nicotinamide;

6-[(2-furylmethyl)amino]-N-[7-methoxy-8-(3-morpholin-4-ylpropoxy)-2,3-dihydroimidazo[1,2-c]quinazolin-5-yl]nicotinamide;

6-[(2-methoxyethyl)amino]-N-[7-methoxy-8-(3-morpholin-4-ylpropoxy)-2,3-dihydroimidazo[1,2-c]quinazolin-5-yl]nicotinamide;

N-[7-methoxy-8-(3-morpholin-4-ylpropoxy)-2,3-dihydroimidazo[1,2-c]quinazolin-5-yl]-6-(1H-pyrrol-1-yl)nicotinamide;

N-[7-methoxy-8-(3-morpholin-4-ylpropoxy)-2,3-dihydroimidazo[1,2-c]quinazolin-5-yl]-6-morpholin-4-ylnicotinamide;

N-{7-methoxy-8-[3-(methylamino)propoxy]-2,3-dihydroimidazo[1,2-c]quinazolin-5-yl}nicotinamide;

6-[(2,2-dimethylpropanoyl)amino]-N-[7-methoxy-8-(3-morpholin-4-ylpropoxy)-2,3-dihydroimidazo[1,2-c]quinazolin-5-yl]nicotinamide;

6-[(cyclopropylcarbonyl)amino]-N-[7-methoxy-8-(3-morpholin-4-ylpropoxy)-2,3-dihydroimidazo[1,2-c]quinazolin-5-yl]nicotinamide N-[7-methoxy-8-(3-morpholin-4-ylpropoxy)-2,3-dihydroimidazo[1,2-c]quinazolin-5-yl]-6-(2,2,2-trifluoroethoxy)nicotinamide;

N-[7-methoxy-8-(3-morpholin-4-ylpropoxy)-2,3-dihydroimidazo[1,2-c]quinazolin-5-yl]-6-(trifluoromethyl)nicotinamide;

6-(isobutyrylamino)-N-[7-methoxy-8-(3-morpholin-4-ylpropoxy)-2,3-dihydroimidazo[1,2-c]quinazolin-5-yl]nicotinamide;

N-{7-methoxy-8-[3-(4-methylpiperazin-1-yl)propoxy]-2,3-dihydroimidazo[1,2-c]quinazolin-5-yl}nicotinamide;

N-[7-methoxy-8-(3-morpholin-4-ylpropoxy)-2,3-dihydroimidazo[1,2-c]quinazolin-5-yl]-2-{[(methylamino)carbonyl]amino}-1,3-thiazole-4-carboxamide;

N-[7-methoxy-8-(3-morpholin-4-ylpropoxy)-2,3-dihydroimidazo[1,2-c]quinazolin-5-yl]-6-{[(methylamino)carbonyl]amino}nicotinamide;

N-[7-methoxy-8-(3-morpholin-4-ylpropoxy)-2,3-dihydroimidazo[1,2-c]quinazolin-5-yl]-2-(methylamino)-1,3-thiazole-4-carboxamide;

N-[7-methoxy-8-(2-morpholin-4-ylethoxy)-2,3-dihydroimidazo[1,2-c]quinazolin-5-yl]nicotinamide;

N-{8-[2-(dimethylamino)ethoxy]-7-methoxy-2,3-dihydroimidazo[1,2-c]quinazolin-5-yl}-2,4-dimethyl-1,3-thiazole-5-carboxamide;

N-{8-[2-(dimethylamino)ethoxy]-7-methoxy-2,3-dihydroimidazo[1,2-c]quinazolin-5-yl}-6-methylnicotinamide;

6-{[(isopropylamino)carbonyl]amino}-N-[7-methoxy-8-(3-morpholin-4-ylpropoxy)-2,3-dihydroimidazo[1,2-c]quinazolin-5-yl]nicotinamide;

N-[7-methoxy-8-(3-morpholin-4-ylpropoxy)-2,3-dihydroimidazo[1,2-c]quinazolin-5-yl]-6-pyrrolidin-1-ylnicotinamide;

6-(dimethylamino)-N-[7-methoxy-8-(3-morpholin-4-ylpropoxy)-2,3-dihydroimidazo[1,2-c]quinazolin-5-yl]nicotinamide;

N-[7-methoxy-8-(3-piperidin-1-ylpropoxy)-2,3-dihydroimidazo[1,2-c]quinazolin-5-yl]nicotinamide;

N-[7-methoxy-8-(2-pyrrolidin-1-ylethoxy)-2,3-dihydroimidazo[1,2-c]quinazolin-5-yl]nicotinamide;

N-[7-methoxy-8-(2-piperidin-1-ylethoxy)-2,3-dihydroimidazo[1,2-c]quinazolin-5-yl]nicotinamide;

6-{[(ethylamino)carbonyl]amino}-N-[7-methoxy-8-(3-morpholin-4-ylpropoxy)-2,3-dihydroimidazo[1,2-c]quinazolin-5-yl]nicotinamide;

6-fluoro-N-[7-methoxy-8-(3-morpholin-4-ylpropoxy)-2,3-dihydroimidazo[1,2-c]quinazolin-5-yl]nicotinamide;
2-amino-N-[7-methoxy-8-(3-morpholin-4-ylpropoxy)-2,3-dihydroimidazo[1,2-c]quinazolin-5-yl]-1,3-oxazole-4-carboxamide;
2-(ethylamino)-N-[7-methoxy-8-(3-morpholin-4-ylpropoxy)-2,3-dihydroimidazo[1,2-c]quinazolin-5-yl]-1,3-thiazole-4-carboxamide;
N-[7-methoxy-8-(3-morpholin-4-ylpropoxy)-2,3-dihydroimidazo[1,2-c]quinazolin-5-yl]pyrazine-2-carboxamide;
N-[8-(2-aminoethoxy)-7-methoxy-2,3-dihydroimidazo[1,2-c]quinazolin-5-yl]nicotinamide;
6-amino-N-[7-methoxy-8-(3-morpholin-4-ylpropoxy)-2,3-dihydroimidazo[1,2-c]quinazolin-5-yl]nicotinamide;
N-[7-methoxy-8-(3-morpholin-4-ylpropoxy)-2,3-dihydroimidazo[1,2-c]quinazolin-5-yl]isonicotinamide;
N-{8-[3-(diethylamino)propoxy]-7-methoxy-2,3-dihydroimidazo[1,2-c]quinazolin-5-yl}nicotinamide;
N-{8-[2-(diisopropylamino)ethoxy]-7-methoxy-2,3-dihydroimidazo[1,2-c]quinazolin-5-yl}nicotinamide;
N-{8-[2-(diethylamino)ethoxy]-7-methoxy-2,3-dihydroimidazo[1,2-c]quinazolin-5-yl}nicotinamide;
N-{8-[3-(dimethylamino)propoxy]-7-methoxy-2,3-dihydroimidazo[1,2-c]quinazolin-5-yl}nicotinamide;
N-{8-[2-(dimethylamino)ethoxy]-7-methoxy-2,3-dihydroimidazo[1,2-c]quinazolin-5-yl}nicotinamide;
N-[7-methoxy-8-(3-morpholin-4-ylpropoxy)-2,3-dihydroimidazo[1,2-c]quinazolin-5-yl]-2-(methylamino)pyrimidine-5-carboxamide;
N-[7-methoxy-8-(3-morpholin-4-ylpropoxy)-2,3-dihydroimidazo[1,2-c]quinazolin-5-yl]-2-(methylthio)pyrimidine-5-carboxamide;
N-[8-(3-aminopropoxy)-7-methoxy-2,3-dihydroimidazo[1,2-c]quinazolin-5-yl]nicotinamide trifluoroacetate;
N-[7-methoxy-8-(3-morpholin-4-ylpropoxy)-2,3-dihydroimidazo[1,2-c]quinazolin-5-yl]thiophene-2-carboxamide;
N-[7-methoxy-8-(3-morpholin-4-ylpropoxy)-2,3-dihydroimidazo[1,2-c]quinazolin-5-yl]-2,4-dimethyl-1,3-thiazole-5-carboxamide;
2-methoxy-N-[7-methoxy-8-(3-morpholin-4-ylpropoxy)-2,3-dihydroimidazo[1,2-c]quinazolin-5-yl]pyrimidine-5-carboxamide;
N-[7-methoxy-8-(3-morpholin-4-ylpropoxy)-2,3-dihydroimidazo[1,2-c]quinazolin-5-yl]-3-furamide;
N-[7-methoxy-8-(3-morpholin-4-ylpropoxy)-2,3-dihydroimidazo[1,2-c]quinazolin-5-yl]thiophene-3-carboxamide;
N-[7-methoxy-8-(3-morpholin-4-ylpropoxy)-2,3-dihydroimidazo[1,2-c]quinazolin-5-yl]-2-methyl-1,3-thiazole-4-carboxamide;
6-methoxy-N-[7-methoxy-8-(3-morpholin-4-ylpropoxy)-2,3-dihydroimidazo[1,2-c]quinazolin-5-yl]nicotinamide;
5-methoxy-N-[7-methoxy-8-(3-morpholin-4-ylpropoxy)-2,3-dihydroimidazo[1,2-c]quinazolin-5-yl]nicotinamide;
N-[7-methoxy-8-(3-morpholin-4-ylpropoxy)-2,3-dihydroimidazo[1,2-c]quinazolin-5-yl]-6-methylnicotinamide;
6-(acetylamino)-N-[7-methoxy-8-(3-morpholin-4-ylpropoxy)-2,3-dihydroimidazo[1,2-c]quinazolin-5-yl]nicotinamide;
N-[7-methoxy-8-(3-morpholin-4-ylpropoxy)-2,3-dihydroimidazo[1,2-c]quinazolin-5-yl]nicotinamide;
or a physiologically acceptable salt, solvate, hydrate or stereoisomer thereof.

In another embodiment, said component A is a compound selected from the list consisting of:
N-[7-methoxy-8-(3-morpholin-4-ylpropoxy)-2,3-dihydroimidazo[1,2-c]quinazolin-5-yl]nicotinamide;
N-[7-methoxy-8-(3-morpholin-4-ylpropoxy)-2,3-dihydroimidazo[1,2-c]quinazolin-5-yl]-6-methylnicotinamide;
5-methoxy-N-[7-methoxy-8-(3-morpholin-4-ylpropoxy)-2,3-dihydroimidazo[1,2-c]quinazolin-5-yl]nicotinamide;
N-[7-methoxy-8-(3-morpholin-4-ylpropoxy)-2,3-dihydroimidazo[1,2-c]quinazolin-5-yl]-2,4-dimethyl-1,3-thiazole-5-carboxamide;
N-{8-[2-(dimethylamino)ethoxy]-7-methoxy-2,3-dihydroimidazo[1,2-c]quinazolin-5-yl}nicotinamide;
N-{8-[3-(dimethylamino)propoxy]-7-methoxy-2,3-dihydroimidazo[1,2-c]quinazolin-5-yl}nicotinamide;
6-{[(isopropylamino)carbonyl]amino}-N-[7-methoxy-8-(3-morpholin-4-ylpropoxy)-2,3-dihydroimidazo[1,2-c]quinazolin-5-yl]nicotinamide;
N-{8-[2-(dimethylamino)ethoxy]-7-methoxy-2,3-dihydroimidazo[1,2-c]quinazolin-5-yl}-2,4-dimethyl-1,3-thiazole-5-carboxamide;
N-[7-methoxy-8-(2-morpholin-4-ylethoxy)-2,3-dihydroimidazo[1,2-c]quinazolin-5-yl]nicotinamide;
rel-6-amino-N-(8-{3-[(2R,6S)-2,6-dimethylmorpholin-4-yl]propoxy}-7-methoxy-2,3-dihydroimidazo[1,2-c]quinazolin-5-yl)nicotinamide;
rel-2-amino-N-(8-{3-[(2R,6S)-2,6-dimethylmorpholin-4-yl]propoxy}-7-methoxy-2,3-dihydroimidazo[1,2-c]quinazolin-5-yl)pyrimidine-5-carboxamide;
2-amino-N-[7-methoxy-8-(3-morpholin-4-ylpropoxy)-2,3-dihydroimidazo[1,2-c]quinazolin-5-yl]pyrimidine-5-carboxamide;
N-{8-[2-(dimethylamino)ethoxy]-7-methoxy-2,3-dihydroimidazo[1,2-c]quinazolin-5-yl}pyrimidine-5-carboxamide;
N-[7-methoxy-8-(3-morpholin-4-ylpropoxy)-2,3-dihydroimidazo[1,2-c]quinazolin-5-yl]pyrimidine-5-carboxamide;
or a physiologically acceptable salt, solvate, hydrate or stereoisomer thereof.

In another embodiment, said component A is 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof.

In another embodiment, said component A is 2-amino-N-[7-methoxy-8-(3-morpholin-4-ylpropoxy)-2,3-dihydroimidazo[1,2-c]quinazolin-5-yl]pyrimidine-5-carboxamide dihydrochloride.

Where there is a discrepancy between the chemical name and the chemical structure depicted, the chemical structure depicted takes precedence over the chemical name given.

Without being bound by theory or mechanism, the compounds of the present invention display surprising activity for the inhibition of phosphatidylinositol-3-kinase and chemical and structural stability over those compounds of the prior art. It is believed that this surprising activity is based on the chemical structure of the compounds, in particular the basicity of the compounds as a result of $R^1$ being amino optionally substituted with $R^5$ and $R^{5'}$. Further, the appropriate choice of $R^3$ and $R^2$ provide the necessary activity against the appropriate isoforms to allow for activity in vivo.

The synthesis of the compounds listed above is described in International Patent Application No. PCT/EP2003/010377, published as WO 2004/029055 A1, and in International Patent Application No. PCT/US2007/024985, published as WO 2008/070150, both of which are hereby incorporated herein in their entirety by reference.

Said component A may be in the form of a pharmaceutical formulation which is ready for use to be administered simultaneously, concurrently, separately or sequentially. The components may be administered independently of one another by the oral, intravenous, topical, local installations, intraperitoneal or nasal route.

The PI3K-inhibitors mentioned in the prior art as well as in the lists above have been disclosed for the treatment or prophylaxis of different diseases, especially cancer.

The specific compounds of the lists as disclosed above are preferred as being component A of the combination, most preferred is the compound used in the experimental section.

The synergistic behavior of a combination of the present invention is demonstrated herein with one of the PI3K inhibitors specifically disclosed in the Examples section as compound A.

In addition a combination of the present invention comprising compound A as mentioned above and a pharmaceutically acceptable salt of radium-223 is a preferred aspect of the invention.

In another aspect a combination of the present invention comprises compound A or a pharmaceutically acceptable salt thereof as mentioned above and a pharmaceutically acceptable salt of the alkaline-earth radionuclide radium-223.

In another aspect a combination of the present invention comprises compound A or a pharmaceutically acceptable salt thereof as mentioned above and the dichloride salt of radium-223.

It is to be understood that the present invention relates also to any combination of the embodiments of component A described above.

Component B of the Combination

Component B is a suitable pharmaceutically acceptable salt of the alkaline-earth radionuclide radium-223.

A suitable pharmaceutically acceptable salt of radium-223 can be, for example, an acid addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2 (4 hydroxybenzoyl) benzoic, camphoric, cinnamic, cyclopentanepropionic, digluconic, 3 hydroxy 2 naphthoic, nicotinic, pamoic, pectinic, persulfuric, 3 phenylpropionic, picric, pivalic, 2 hydroxyethanesulfonate, itaconic, sulfamic, trifluoromethanesulfonic, dodecylsulfuric, ethansulfonic, benzenesulfonic, para toluenesulfonic, methansulfonic, 2 naphthalenesulfonic, naphthalinedisulfonic, camphorsulfonic acid, citric, tartaric, stearic, lactic, oxalic, malonic, succinic, malic, adipic, alginic, maleic, fumaric, D gluconic, mandelic, ascorbic, glucoheptanoic, glycerophosphoric, aspartic, sulfosalicylic, hemisulfuric, or thiocyanic acid, for example.

A preferred suitable pharmaceutically acceptable salt of radium-223 is the dichloride ($Ra^{223}Cl_2$).

Methods for preparation of a physiologically acceptable solution comprising radium-223 are disclosed e.g. in WO 2000/40275(A2), WO 2011/134671(A1), and WO 2011/134672(A1).

Physiologically acceptable solutions comprising radium-223 show a unique mechanism of action as a targeted radiopharmaceutical. They represent a new generation of alpha emitting therapeutic pharmaceuticals based on the natural bone-seeking nuclide radium-223.

Preferably, an aqueous solution of radium-223 chloride ($^{223}RaCl2$) for intravenous injection, sterile and free from bacterial endotoxins is used.

Preferably, the solution is isotonic, containing a sodium citrate buffered saline to physiological pH.

A preferred dosage regimen for radium-223 chloride injection is 50 kBq per kg body weight given at 4 week intervals, as a course consisting of 6 injections. Single radium-223 doses up to 250 kBq per kg body weight were evaluated in a phase I clinical trial.

The observed adverse reactions at this dose were diarrhea and reversible myelosuppression (including one case (⅕) of grade 3 neutropenia).

As an example, the aqueous radium-223 dichloride solution may be supplied in a single-dose 10 ml vial which contains a fill volume of 6 ml. This product has a radioactivity concentration of radium-223 of 1,000 kBq/mL (0.03 mCi/mL), corresponding to 0.53 ng/mL of radium at reference date. The active moiety is the alpha particle emitting nuclide radium 223 (half-life is 11.4 days), present as a divalent cation ($^{223}Ra^{2+}$). The fraction of energy emitted from radium-223 and its daughters as alpha-particles is 95.3%, the fraction emitted as beta-particles is 3.6%, and the fraction emitted as gamma-radiation is 1.1%. The combined energy from the emitted radiation from complete decay of radium-223 and its daughter nuclides is 28.2 MeV.

Radium-223 is to be administered intravenously by qualified personnel as a slow bolus injection. An intravenous access line should be used for administration of Radium-223. The line must be flushed with isotonic saline before and after injection of Radium-223.

Radium-223 selectively targets areas of increased bone turnover, as in bone metastases, and concentrates by forming a complex with hydroxyapatite. Alpha emission contributes about 93% of the total radiation absorbed dose. The high linear energy alpha particle radiation induces double-strand DNA breaks, resulting in a potent and localized cytotoxic effect in the target areas containing metastatic cancer cells. The short path length (less than 100 micrometers) of the alpha particles minimizes the effect on adjacent healthy tissue such as the bone marrow.

In accordance with an embodiment, the present invention relates to a combination of any component A mentioned herein with any component B mentioned herein, optionally with any component C mentioned herein.

In one embodiment component A of the combination is the compound used in the experimental section and Component B is radium-223 dichloride ($Ra^{223}Cl_2$) as being used in the experimental section.

In a particular embodiment, the present invention relates to a combination of a component A with a component B, optionally with a component C, as mentioned in the Examples Section herein.

Further, the present invention relates to:
a kit comprising:
  a combination of:
  component A: one or more PI3K-kinase inhibitors, or a physiologically acceptable salt, solvate, hydrate or stereoisomer thereof;
  component B: a suitable pharmaceutically acceptable salt of the alkaline-earth radionuclide radium-223 or a solvate or a hydrate thereof; and, optionally,
  component C: one or more further pharmaceutical agents;
in which optionally either or both of said components A and B in any of the above-mentioned combinations are in the form of a pharmaceutical formulation which is ready for use to be administered simultaneously, concurrently, separately or sequentially.

The term "component C" being at least one pharmaceutical agent includes the effective compound itself as well as its pharmaceutically acceptable salts, solvates, hydrates or stereoisomers as well as any composition or pharmaceutical formulation comprising such effective compound or its pharmaceutically acceptable salts, solvates, hydrates or stereoisomers. A list of such readily available agents is being provided further below.

The components may be administered independently of one another by the oral, intravenous, topical, local installations, intraperitoneal or nasal route.

Component A is administered intravenously, intraperitoneally, preferably it is administered orally.

Component B preferably is administered by the intravenous route.

Component C being administered as the case may be.

The term "pharmaceutically acceptable" is used synonymously to the term "physiologically acceptable".

The term "pharmaceutically or physiologically acceptable salt" of component A refers to a relatively non-toxic, inorganic or organic acid addition salt of a compound of the present invention. For example, see S. M. Berge, et al. "Pharmaceutical Salts," *J. Pharm. Sci.* 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and chorine salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

Representative salts of a component A of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, chloride, bromide, iodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, sulfate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, or butyl chlorides, bromides and iodides; dialkyl sulfates like dimethyl, diethyl, dibutyl sulfate, or diamyl sulfates, long chain halides such as decyl, lauryl, myristyl and strearyl chlorides, bromides and iodides, aralkyl halides like benzyl and phenethyl bromides and others.

A solvate for the purpose of this invention is a complex of a solvent and a compound of the invention in the solid state. Exemplary solvates would include, but are not limited to, complexes of a compound of the invention with ethanol or methanol. Hydrates are a specific form of solvate wherein the solvent is water.

Components of this invention can be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

Components of this invention can also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions can be formulated by suspending the active ingredient in a vegetable oil such as, for example, *arachis* oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs can be formulated with sweetening agents such as, for example, glycerol, propylene glycol, sorbitol or sucrose. Such formulations may also contain a demulcent, and preservative, such as methyl and propyl parabens and flavoring and coloring agents.

Components of this invention can also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions can be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation can also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

Components of the invention can also be administered in the form of suppositories for rectal administration of the drug. These components can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It can be desirable or necessary to introduce a component of the present invention to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)—Part-1" *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC$—$CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to *arachis* oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);
viscosity increasing agents (examples include but are not limited to alginic acid, bentonite, carbomers, carboxymethylcellulose sodium, methylcellulose, polyvinyl pyrrolidone, sodium alginate and tragacanth); and
wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution:
A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilized Powder for IV Administration:
A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular Suspension:
The following solution or suspension can be prepared, for intramuscular injection:
50 mg/mL of the desired, water-insoluble compound of this invention
5 mg/mL sodium carboxymethylcellulose
4 mg/mL TWEEN 80
9 mg/mL sodium chloride
9 mg/mL benzyl alcohol Hard Shell Capsules:
A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:
A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets:
A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules:
These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Commercial Utility

Component A
The compounds of formula (A) and (I) and the stereoisomers thereof according to the combination as referred to above are components A. The compounds according to the combination have valuable pharmaceutical properties, which make them commercially utilizable. In particular, they inhibit the PI3K/AKT pathway and exhibit cellular activity. They are expected to be commercially applicable in the therapy of diseases (e.g. diseases dependent on overactivated PI3K/AKT). An abnormal activation of the PI3K/AKT pathway is an essential step towards the initiation and maintenance of human tumors and thus its inhibition, for example with PI3K inhibitors, is understood to be a valid approach for treatment of human tumors. For a recent review see Garcia-Echeverria et al (Oncogene, 2008, 27, 551-5526.

Component B
Due to the mechanism as discussed in the introductory section component B is especially suitable to have effects on tumor diseases, especially those developing metastases in bones.

Combination
The combinations of the present invention thus can be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses, such as, for example, haematological tumours and/or metastases thereof, solid tumours, and/or metastases thereof, e.g. leukaemias, multiple myeloma thereof and myelodysplastic syndrome, malignant lymphomas, breast tumours including and bone metastases thereof, tumours of the thorax including non-small cell and small cell lung tumours and bone metastases thereof, gastrointestinal tumours, endocrine tumours, mammary and other gynaecological tumours and bone metastases thereof, urological tumours including renal, bladder and prostate tumours, skin tumours, and sarcomas, and/or metastases thereof.

One embodiment relates to the use of a combination according to any one of claims 1 to 12 for the preparation of a medicament for the treatment or prophylaxis of a cancer, particularly breast cancer, prostate cancer, multiple myeloma, hepatocyte carcinoma, lung cancer, in particular non-small cell lung carcinoma, colorectal cancer, melanoma, pancreatic cancer and/or metastases thereof.

In one embodiment the invention relates to combinations comprising component A or a pharmaceutically acceptable salt thereof and Component B being a pharmaceutically acceptable salt of the alkaline earth radionuclide radium-223 for use in the treatment of cancer indications particularly for such cancer type which is known to form metastases in bone.

Such cancer types are e.g. breast, prostate, lung, multiple myeloma, kidney or thyroid cancer.

Another embodiment relates to the use of a combination according to the present invention for the preparation of a medicament for the treatment or prophylaxis of breast cancer, prostate cancer, multiple myeloma, non-small cell lung cancer and/or metastases thereof, especially wherein the metastases are bone metastases.

In one embodiment the invention relates to a method of treatment or prophylaxis of a cancer, particularly breast cancer, prostate cancer, multiple myeloma, hepatocyte carcinoma, lung cancer, in particular non-small cell lung carcinoma, colorectal cancer, melanoma, or pancreatic cancer, in a subject, comprising administering to said subject a therapeutically effective amount of a combination according to any one of claims 1 to 12.

In another embodiment the invention relates to a method of treatment or prophylaxis of a cancer, particularly breast cancer, prostate cancer, multiple myeloma, hepatocyte carcinoma, lung cancer, in particular non-small cell lung carcinoma, colorectal cancer, melanoma, or pancreatic cancer, in a subject, comprising administering to said subject a therapeutically effective amount of a combination according to any one of claims 1 to 12.

In another embodiment the invention relates to a method of treatment or prophylaxis of a cancer, particularly breast cancer, prostate cancer, multiple myeloma, hepatocyte carcinoma, lung cancer, in particular non-small cell lung carcinoma, colorectal cancer, melanoma, or pancreatic cancer and/or metastases thereof in a subject, comprising administering to said subject a therapeutically effective amount of a combination according to any one of claims 1 to 12.

Preferred uses of the combinations of the invention are the treatment of multiple myeloma, lung, breast and prostate cancer, especially castration-resistant prostate cancer (CRPC), and bone metastases.

One preferred embodiment is the use of the combinations of the invention for the treatment of prostate cancer, especially castration-resistant prostate cancer (CRPC) and bone metastases.

One preferred embodiment is the use of the combinations of the invention for the treatment of breast cancer and bone metastases.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Combinations of the present invention might be utilized to inhibit, block, reduce, decrease, etc., cell proliferation and/or cell division, and/or produce apoptosis.

This invention includes a method comprising administering to a mammal in need thereof, including a human, an amount of a component A and an amount of component B of this invention, or a pharmaceutically acceptable salt, isomer, polymorph, metabolite, hydrate, solvate or ester thereof; etc. which is effective to treat the disorder.

Hyper-proliferative disorders include but are not limited, e.g., psoriasis, keloids, and other hyperplasias affecting the skin, benign prostate hyperplasia (BPH), as well as malignant neoplasia. Examples of malignant neoplasia treatable with the compounds according to the present invention include solid and hematological tumors. Solid tumors can be exemplified by tumors of the breast, bladder, bone, brain, central and peripheral nervous system, colon, anum, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasias include inherited cancers exemplified by Retinoblastoma and Wilms tumor. In addition, malignant neoplasias include primary tumors in said organs and corresponding secondary tumors in distant organs ("tumor metastases"). Hematological tumors can be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

Examples of breast cancer include, but are not limited to invasive ductal carcinoma, invasive lobular carcinoma, ductal carcinoma in situ, and lobular carcinoma in situ, particularly with bone metastases.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Combinations of the present invention might also be used for treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer. Thus, combinations of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Component A

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredients to be administered in the treatment of one of these conditions can vary widely according to such considerations as the particular component And dosage unit employed, the mode of administration, the period of treatment, the age and sex of the patient treated, and the nature and extent of the condition treated.

The total amount of the active ingredients to be administered will generally range from about 0.001 mg/kg to about 200 mg/kg body weight per day, and preferably from about 0.01 mg/kg to about 20 mg/kg body weight per day. Clinically useful dosing schedules of a compound will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Component B

A preferred dosage regimen for radium-223 injection is 50 kBq per kg body weight given at 4 week intervals, as a course consisting of 6 injections. Single radium-223 doses up to 250 kBq per kg body weight were evaluated in a phase I clinical trial. The observed adverse reactions at this dose were diarrhea and reversible myelosuppression (including one case (⅕) of grade 3 neutropenia).

As an example, the aqueous radium-223 dichloride solution may be supplied in a single-dose 10 ml vial which contains a fill volume of 6 ml. This product has a radioactivity concentration of radium-223 of 1,000 kBq/mL (0.03 mCi/mL), corresponding to 0.53 ng/mL of radium at reference date.

Radium-223 is to be administered intravenously by qualified personnel as a slow bolus injection. An intravenous access line should be used for administration of Radium-223. The line must be flushed with isotonic saline before and after injection of Radium-223.

Of course the specific initial and continuing dosage regimen for each patient will vary according to the nature and severity of the condition as determined by the attending diagnostician, the activity of the specific compounds employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combinations of the Present Invention

The combinations of the present invention can be used in particular in therapy and prevention, i.e. prophylaxis, of tumour growth and metastases, especially in solid tumours of all indications and stages with or without pre-treatment of the tumour growth, more especially those tumor types spreading into bones.

Methods of testing for a particular pharmacological or pharmaceutical property are well known to persons skilled in the art.

The combinations of component A and component B of this invention can be administered as the sole pharmaceutical agent or in combination with one or more further pharmaceutical agents C where the resulting combination of components A, B and C causes no unacceptable adverse effects. For example, the combinations of components A and B of this invention can be combined with component C, i.e. one or more further pharmaceutical agents, such as known anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agents, and the like, as well as with admixtures and combinations thereof.

Component C, can be one or more pharmaceutical agents such as 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 1143269, BAY 1000394, belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, refametinib, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin. or combinations thereof.

Alternatively, said component C can be one or more further pharmaceutical agents selected from gemcitabine, paclitaxel, cisplatin, carboplatin, sodium butyrate, 5-FU, doxirubicin, tamoxifen, etoposide, trastumazab, gefitinib, intron A, rapamycin, 17-AAG, U0126, insulin, an insulin derivative, a PPAR ligand, a sulfonylurea drug, an α-glucosidase inhibitor, a biguanide, a PTP-1B inhibitor, a DPP-IV inhibitor, a 11-beta-HSD inhibitor, GLP-1, a GLP-1 derivative, GIP, a GIP derivative, PACAP, a PACAP derivative, secretin or a secretin derivative.

Optional anti-hyper-proliferative agents which can be added as component C to the combination of components A and B of the present invention include but are not limited to compounds listed on the cancer chemotherapy drug regimens in the 11$^{th}$ Edition of the *Merck Index*, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use as component C with the combination of components A and B of the present invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel (when component B is not itself paclitaxel), pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use as component C with the combination of components A and B of the present invention include but are not limited to other anti-cancer agents such as epothilone and its derivatives, irinotecan, raloxifen and topotecan.

Generally, the use of cytotoxic and/or cytostatic agents as component C in combination with a combination of components A and B of the present invention will serve to:

(1) yield better efficacy in reducing the growth of a tumor and/or metastasis or even eliminate the tumor and/or metastasis as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (8) provide a longer time for tumor progression, and/or (9) yield efficacy and tolerability results at least as good as those of the agents used alone, compared to known instances where other cancer agent combinations produce antagonistic effects.

EXPERIMENTAL SECTION

Examples Demonstrating the Synergistic Effect of the Combinations of Components A and B of the Present Invention Component A:

In this Experimental section and in the Figures, the term "compound A" is an example of component A and is compound Example 13 of WO 2008/070150 A1 as shown herein: it is 2-amino-N-[7-methoxy-8-(3-morpholin-4-yl-propoxy)-2,3-dihydroimidazo[1,2-c]quinazolin-5-yl]pyrimidine-5-carboxamide, of structure:

compound A or a solvate, hydrate or stereoisomer thereof.

In this Experimental Section and in the Figures, the term "compound A'" refers to 2-amino-N-[7-methoxy-8-(3-morpholin-4-ylpropoxy)-2,3-dihydroimidazo[1,2-c]quinazolin-5-yl]pyrimidine-5-carboxamide dihydrochloride, of structure:

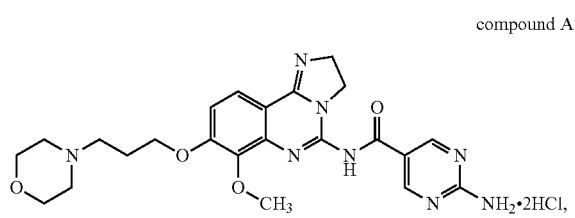

compound A' or a solvate, hydrate or stereoisomer thereof.

The synthesis of compound A' is described in European patent application number EP 11 161 111.7, and in PCT application number PCT/EP2012/055600 published under WO 2012/136553, both of which are hereby incorporated herein in their entirety by reference.

Component B:

In this Experimental Section and in the Figures, the term "compound B" or "alpharadin" refers to radium-223 dichloride, the synthesis of which is disclosed in WO2000/040275, which is incorporated herein in its entirety by reference.

Examples Demonstrating the Synergistic Effect of the Combinations of Compound A' and Compound B of the Present Invention The effects of PI3K inhibitor compound A' and compound B in MCF-7 and 4T1 breast cancer cells and PC-3 and LNCaP prostate cancer cells were investigated in vitro as single agent and in combination. The effects were studied by measuring cell proliferation and apoptosis. Compound B and the reference inhibitor doxorubicin were added at day 0. The PI3K inhibitors were added at day −1 (24 hours before addition of Alpharadin) and at day 4. The following two concentrations of the inhibitors and two concentrations of radium 223 in 4 replicates were tested:

TABLE 1

| Cell line | Dose 1 | Dose 2 |
|---|---|---|
| | Compound A' | |
| MCF-7 | 50 nM | 500 nM |
| 4T1 | 100 nM | 1000 nM |
| PC-3 | 50 nM | 500 nM |
| LNCaP | 100 nM | 1000 nM |
| | Compound B | |
| MCF-7 | 1600 Bq/ml | 800 Bq/ml |
| 4T1 | 1600 Bq/ml | 800 Bq/ml |
| PC-3 | 1600 Bq/ml | 800 Bq/ml |
| LNCaP | 1600 Bq/ml | 400 Bq/ml |

The effects on cell proliferation were studied using a WST-1 based proliferation assay and the effects on apoptosis were studied in parallel plates by measuring caspase 3/7 activity. The measurements were performed at 4 different time points, days 1, 2, 3 and 5. Caspase activity was normalized to the cell number obtained with the WST-1 assay in parallel plates.

The reference compound doxorubicin inhibited proliferation in all tested cell lines; MCF-7, 4T1, PC-3 and LNCaP, describing that the assays were performed successfully and the results obtained are reliable.

DESCRIPTION OF THE FIGURES

Compound A' is a PI3K inhibitor as mentioned above.

TABLE 2

Figure 1:
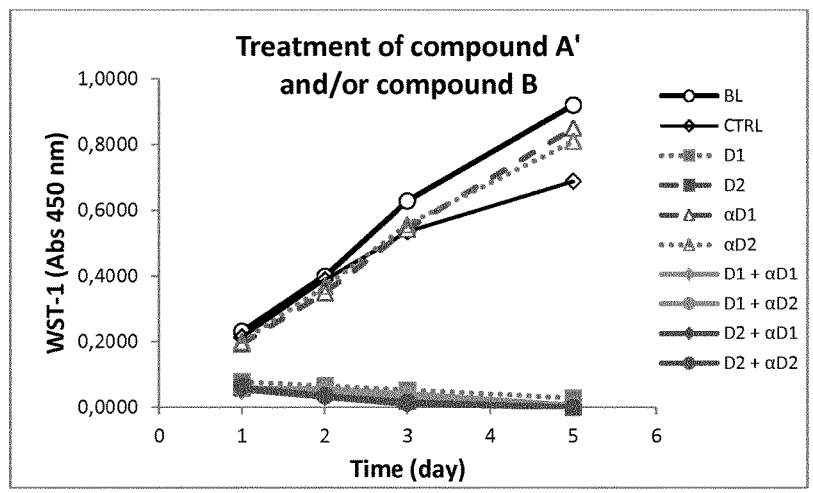
Figure 1:
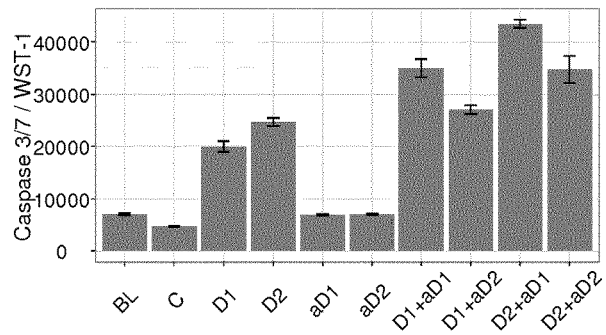
Figure 2:
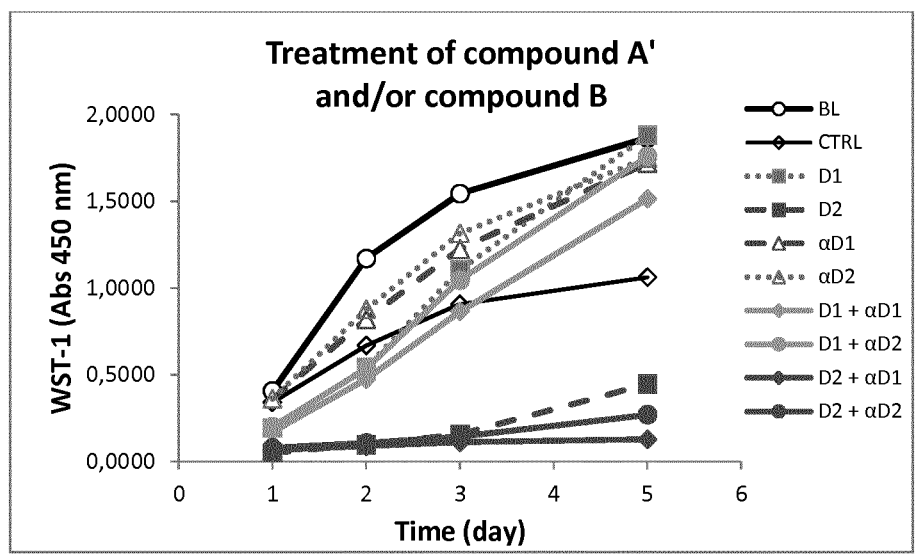
Figure 3:
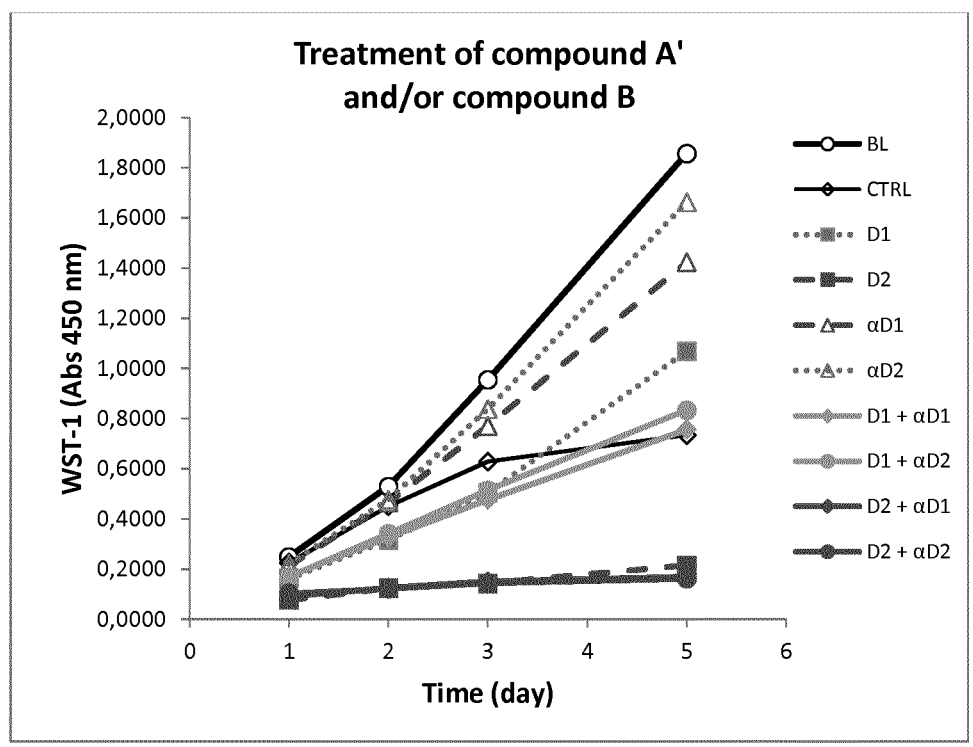
Figure 4:
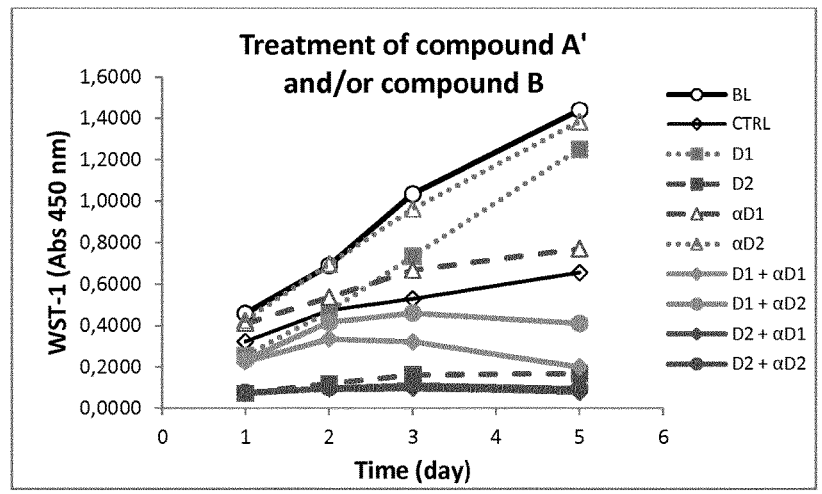
Figure 4:
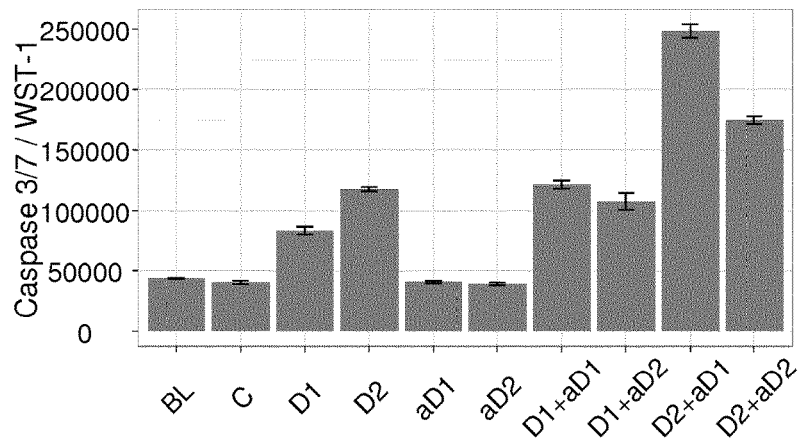

| Cell line | Description | Derived from | Pathway Mutation |
|---|---|---|---|
| MCF-7 | human mammary gland adenocarcinoma | pleural effusion | PIK3CA |
| 4T1 | mouse mammary gland adenocarcinoma | mammary tumor | |
| PC-3 | human prostate adenocarcinoma | bone | PTEN-del |
| LNCaP | human prostate carcinoma | left supraclavicular lymph node | PTEN-del |

FIG. 1/4

The effects of compound A' and compound B on MCF-7 cell proliferation at days 1-5 and apoptosis induction at day 2.

(A) The results are shown as Absorbance (450 nm) measured in the WST-1 proliferation assay (MEAN). (B) The results are shown as Caspase 3/7/WST-1 values (MEAN). The results of the control group doxorubicin (C), Compound A' groups (D1=50 nM and D2=500 nM) and compound B groups (aD1=1600 Bq/ml and aD2=800 Bq/ml) were compared to the baseline group. (B) The effects of PI3K inhibitor compound A' and Radium 223 on MCF-7 cell caspase 3/7 activity at days 2. The results are shown as Caspase 3/7/WST-1 values (MEAN+SEM). The results of the control group (C), PI3K inhibitor groups (D1 and D2) or Radium 223 groups (aD1 and aD2), and the corresponding combo groups (D1+aD1, D1+aD2, D2+aD1 and D2+aD2) are depicted.

FIG. 2/4

The effects of compound A' and compound B on 4T1 breast tumor cell proliferation at days 1-5.

The results are shown as Absorbance (450 nm) measured in the WST-1 proliferation assay (MEAN). The results of the control group doxorubicin (C), compound A' groups (D1=100 nM and D2=1000 nM) and compound B groups (aD1=1600 Bq/ml and aD2=800 Bq/ml) and the corresponding combo groups (D1+aD1, D1+aD2, D2+aD1 and D2+aD2) are depicted.

FIG. 3/4

The effects of compound A' and compound B on PC3 prostate tumor cell proliferation at days 1-5.

The results are shown as Absorbance (450 nm) measured in the WST-1 proliferation assay (MEAN). The results of the control group doxorubicin (C), compound A' groups (D1=50 nM and D2=500 nM) and compound B groups (aD1=1600 Bq/ml and aD2=800 Bq/ml) and the corresponding combo groups (D1+aD1, D1+aD2, D2+aD1 and D2+aD2) are depicted.

FIG. 4/4

The effects of compound A' and compound B on LNCaP prostate tumor cell proliferation at days 1-5 and apoptosis induction at day 2.

(A) The results are shown as Absorbance (450 nm) measured in the WST-1 proliferation assay (MEAN). (B) The results are shown as Caspase 3/7/WST-1 values (MEAN+SEM). The results of the control group doxorubicin (C), compound A' groups (D1=100 nM and D2=1000 nM) and compound B groups (aD1=1600 Bq/ml and aD2=800 Bq/ml) and the corresponding combo groups (D1+aD1, D1+aD2, D2+aD1 and D2+aD2) are depicted.

CONCLUSIONS

In MCF7, a breast cancer cell line with ER+ and activating PIK3CA mutation, compound B showed only slight inhibition of tumor cell proliferation, while compound A' showed potent anti-proliferative activity. Combination of compound A' and compound B further enhanced the anti-proliferative effect. Monotherapy of compound B could not induce tumor cell death, while compound A' only at high dose can induce apoptosis and tumor killing effects were further enhanced by combination with compound B.

In 4T1, a triple negative metastatic breast cancer cell line, compound B and compound A' at lower (100 nM) dose showed only moderate inhibition of tumor cell proliferation, while compound B at higher dose showed strong anti-proliferative effects. Combination of compound A' and compound B showed synergistic effects.

In PC3, a AR-negative CRPC cell line with loss-of-function of tumor suppressor PTEN, compound B showed moderate inhibition of tumor cell proliferation and better anti-proliferactive activity was observed with compound A'. All the combination groups showed synergistic effects compared to the corresponding monotherapy groups.

In LNCaP, a AR-positive CRPC cell line with loss-of-function of tumor suppressor PTEN, compound B was effective at high dose (1600 Bq/mL) and compound A' showed strong anti-proliferative effects. Combination of compound A' and compound B at the low doses (100 nM and 800 Bq/mL) showed synergistic anti-proliferative effects. Although the synergistic anti-proliferative effects could not be demonstrated in the high dose combination group due to potent single agent activity of compound A', strong synergy was observed in caspase 3/7 apoptosis assay in both dose groups.

Taken together, combination of compound A' and compound B demonstrated direct and synergistic anti-tumor activity in all 4 breast and prostate tumor cell lines tested, synergistic induction of tumor cell death was also observed in hormone receptor positive MCF7 (ER+) breast cancer and LNCaP (AR+) prostate tumor cell lines.

In summary, our data indicate synergistic effects of the PI3K inhibitor compound A' and compound B in inhibiting tumor cell proliferation and survival, and warrant further clinical evaluation of this promising combination therapy for the treatment of cancer, including breast and prostate cancer and their bone metastases.

REFERENCES

1. Marone, R.; Cmiljanovic, V.; Giese, B.; Wymann, M. P. Targeting phosphoinositide 3-kinase—moving towards therapy. *Biochim. Biophys. Acta, Proteins Proteomics* 2008, 1784, 159-185.
2. Yuan, T. L.; Cantley, L. C. PI3K pathway alterations in cancer: variations on a theme. *Oncogene* 2008, 27, 5497-5510.
3. Manning, B. D.; Cantley, L. C. AKT/PKB signaling: navigating downstream. *Cell* 2007, 129, 1261-1274.
4. Obenauer, J. C.; Cantley, L. C.; Yaffe, M. B. Scansite 2.0: proteome-wide prediction of cell signaling interactions using short sequence motifs. *Nucleic Acids Res.* 2003, 31, 3635-3641.
5. Nicholson, K. M.; Anderson, N. G. The protein kinase B/Akt signalling pathway in human malignancy. *Cell. Signalling* 2002, 14, 381-395.
6. Datta, S. R.; Dudek, H.; Tao, X.; Masters, S.; Fu, H.; Gotoh, Y.; Greenberg, M. E. Akt phosphorylation of BAD couples survival signals to the cell-intrinsic death machinery. *Cell* 1997, 91, 231-241.
7. Zha, J.; Harada, H.; Yang, E.; Jockel, J.; Korsmeyer, S. J. Serine phosphorylation of death agonist BAD in response to survival factor results in binding to 14-3-3 not BCL-XL. *Cell* 1996, 87, 619-628.
8. Romashkova, J. A.; Makarov, S. S. Nf-kB is a target of Akt in anti-apoptotic PDGF signalling. *Nature* 1999, 401, 86-90.
9. Zhou, B. P.; Liao, Y.; Xia, W.; Spohn, B.; Lee, M.-H.; Hung, M.-C. Cytoplasmic localization of p21Cip1/WAF1 by Akt-induced phosphorylation in HER-2/neu-overexpressing cells. *Nat. Cell Biol.* 2001, 3, 245-252.
10. Tran, H.; Brunet, A.; Grenier, J. M.; Datta, S. R.; Fornace, A. J., Jr.; DiStefano, P. S.; Chiang, L. W.; Greenberg, M. E. DNA repair pathway stimulated by the Forkhead Transcription Factor FOXO3a through the Gadd45 protein. *Science* 2002, 296, 530-534.
11. Okumura, E.; Fukuhara, T.; Yoshida, H.; Hanada, S.-I.; Kozutsumi, R.; Mori, M.; Tachibana, K.; Kishimoto, T. Akt inhibits Myt1 in the signalling pathway that leads to meiotic G2/M-phase transition. *Nat. Cell Biol.* 2002, 4, 111-116.
12. Alessi, D. R.; Pearce, L. R.; Garcia-Martinez, J. M. New insights into mTOR signaling: mTORC2 and beyond. *Sci. Signal.* 2009, 2, pe27.
13. Yang, Q.; Guan, K.-L. Expanding mTOR signaling. *Cell Res.* 2007, 17, 666-681.
14. Sarbassov, D. D.; Guertin, D. A.; Ali, S. M.; Sabatini, D. M. Phosphorylation and Regulation of Akt/PKB by the Rictor-mTOR Complex. *Science* 2005, 307, 1098-1101.
15. Harrington, L. S.; Findlay, G. M.; Gray, A.; Tolkacheva, T.; Wigfield, S.; Rebholz, H.; Barnett, J.; Leslie, N. R.; Cheng, S.; Shepherd, P. R.; Gout, I.; Downes, C. P.; Lamb, R. F. The TSC1-2 tumor suppressor controls insulin-PI3K signaling via regulation of IRS proteins. *J. Cell Biol.* 2004, 166, 213-223.
16. Barone, I.; Cui, Y.; Herynk, M. H.; Corona-Rodriguez, A.; Giordano, C.; Selever, J.; Beyer, A.; Ando, S.; Fuqua, S. A. W. Expression of the K303R estrogen receptor-a breast cancer mutation induces resistance to an aromatase inhibitor via addiction to the PI3K/Akt kinase pathway. *Cancer Res.* 2009, 69, 4724-4732.
17. Jozwiak, J.; Jozwiak, S.; Wlodarski, P. Possible mechanisms of disease development in tuberous sclerosis. *Lancet Oncol.* 2008, 9, 73-79.
18. Pearce, L. R.; Komander, D.; Alessi, D. R. The nuts and bolts of AGC protein kinases. *Nat. Rev. Mol. Cell Biol.* 2010, 11, 9-22.
19. Vasudevan, K. M.; Barbie, D. A.; Davies, M. A.; Rabinovsky, R.; McNear, C. J.; Kim, J. J.; Hennessy, B. T.; Tseng, H.; Pochanard, P.; Kim, S. Y.; Dunn, I. F.; Schinzel, A. C.; Sandy, P.; Hoersch, S.; Sheng, Q.; Gupta, P. B.; Boehm, J. S.; Reiling, J. H.; Silver, S.; Lu, Y.; Stemke-Hale, K.; Dutta, B.; Joy, C.; Sahin, A. A.; Gonzalez-Angulo, A. M.; Lluch, A.; Rameh, L. E.; Jacks, T.; Root, D. E.; Lander, E. S.; Mills, G. B.; Hahn, W. C.; Sellers, W. R.; Garraway, L. A. AKT-independent signaling downstream of oncogenic PIK3CA mutations in human cancer. *Cancer Cell* 2009, 16, 21-32.
20. Vanhaesebroeck, B.; Guillermet-Guibert, J.; Graupera, M.; Bilanges, B. The emerging mechanisms of isoform-specific PI3K signaling. *Nat. Rev. Mol. Cell Biol.* 2010, 11, 329-341.
21. Zhao, J. J.; Cheng, H.; Jia, S.; Wang, L.; Gjoerup, O. V.; Mikami, A.; Roberts, T. M. The p110a isoform of PI3K is essential for proper growth factor signaling and oncogenic transformation. *Proc. Natl. Acad. Sci. U.S.A* 2006, 103, 16296-16300.
22. Jia, S.; Liu, Z.; Zhang, S.; Liu, P.; Zhang, L.; Lee, S. H.; Zhang, J.; Signoretti, S.; Loda, M.; Roberts, T. M.; Zhao, J. J. Essential roles of PI(3)K-p110b in cell growth, metabolism and tumorigenesis. *Nature* 2008, 454, 776-779.
23. Vogt, P. K.; Gymnopoulos, M.; Hart, J. R. PI 3-kinase and cancer: changing accents. *Curr. Opin. Genet. Dev.* 2009, 19, 12-17.
24. Jia, S.; Roberts, T. M.; Zhao, J. J. Should individual PI3 kinase isoforms be targeted in cancer?*Curr. Opin. Cell Biol.* 2009, 21, 199-208.
25. Sanger Institute. Sanger Database.
26. Tannock, I. F.; de Wit, R.; Berry, W. R.; Horti, J.; Pluzanska, A.; Chi, K. N.; Oudard, S.; Theodore, C.; James, N. D.; Turesson, I.; Rosenthal, M. A.; Eisenberger, M. A. Docetaxel plus prednisone or mitoxantrone plus prednisone for advanced prostate cancer. *N. Engl. J. Med.* 2004, 351, 1502-1512.
27. Benistant, C.; Chapuis, H.; Roche, S. A specific function for phosphatidylinositol 3-kinase a (p85a-p110a) in cell survival and for phosphatidylinositol 3-kinase b (p85a-p110b) in de novo DNA synthesis of human colon carcinoma cells. *Oncogene* 2000, 19, 5083-5090.
28. Brugge, J.; Hung, M.-C.; Mills, G. B. A new mutational aktivation in the PI3K pathway. *Cancer Cell* 2007, 12, 104-107.
29. Lee, S. H.; Poulogiannis, G.; Pyne, S.; Jia, S.; Zou, L.; Signoretti, S.; Loda, M.; Cantley, L. C.; Roberts, T. M. A constitutively activated form of the p110b isoform of PI3-kinase induces prostatic intraepithelial neoplasia in mice. *Proc. Natl. Acad. Sci. U. S. A.* 2010, 107, 11002-11007, 511002/11001-511002/11050.
30. Wee, S.; Wiederschain, D.; Maira, S.-M.; Loo, A.; Miller, C.; de Beaumont, R.; Stegmeier, F.; Yao, Y.-M.; Lengauer, C. PTEN-deficient cancers depend on PIK3CB. *Proc. Natl. Acad. Sci. U.S.A* 2008, 105, 13057-13062.
31. Liu, P.; Cheng, H.; Roberts, T. M.; Zhao, J. J. Targeting the phosphoinositide 3-kinase pathway in cancer. *Nat. Rev. Drug Disc.* 2009, 8, 627-644.
32. Byun, D.-S.; Cho, K.; Ryu, B.-K.; Lee, M.-G.; Park, J.-I.; Chae, K.-S.; Kim, H.-J.; Chi, S.-G. Frequent monoallelic deletion of PTEN and its reciprocal association with PIK3CA amplification in gastric carcinoma. *Int. J. Cancer* 2003, 104, 318-327.
33. Oki, E.; Kakeji, Y.; Baba, H.; Tokunaga, E.; Nakamura, T.; Ueda, N.; Futatsugi, M.; Yamamoto, M.; Ikebe, M.; Maehara, Y. Impact of loss of heterozygosity of encoding phosphate and tensin homolog on the prognosis of gastric cancer. *J. Gastroenterol. Hepatol.* 2006, 21, 814-818.
34. Li, Y.-L.; Tian, Z.; Wu, D.-Y.; Fu, B.-Y.; Xin, Y. Loss of heterozygosity on 10q23.3 and mutation of tumor suppressor gene PTEN in gastric cancer and precancerous lesions. *World J. Gastroenterol.* 2005, 11, 285-288.
35. Marques, M.; Kumar, A.; Poveda, A. M.; Zuluaga, S.; Hernandez, C.; Jackson, S.; Pasero, P.; Carrera, A. C. Specific function of phosphoinositide 3-kinase beta in the control of DNA replication. *Proc. Natl. Acad. Sci. U.S.A* 2009, 106, 7525-7530.
36. Sujobert, P.; Bardet, V.; Cornillet-Lefebvre, P.; Hayflick, J. S.; Prie, N.; Verdier, F.; Vanhaesebroeck, B.; Muller, O.; Pesce, F.; Ifrah, N.; Hunault-Berger, M.; Berthou, C.; Villemagne, B.; Jourdan, E.; Audhuy, B.; Solary, E.; Witz, B.; Harousseau, J. L.; Himberlin, C.; Lamy, T.; Lioure, B.; Cahn, J. Y.; Dreyfus, F.; Mayeux, P.; Lacombe, C.; Bouscary, D. Essential role for the p110d isoform in phosphoinositide 3-kinase activation and cell proliferation in acute myeloid leukemia. *Blood* 2005, 106, 1063-1066.
37. Bruland O. S., Nilsson S., Fisher D. R., et al., High-linear energy transfer irradiation targeted to skeletal metastases by the alpha-emitter $^{223}$Ra: adjuvant or alternative to conventional modalities?, Clin. Cancer Res. 2006; 12: 6250s-7s.
38. Henriksen G., Breistol K., Bruland O. S., et al., *Significant antitumor effect from bone-seeking, alpha-particle-emitting (223)Ra demonstrated in an experimental skeletal metastases model*, Cancer Res. 2002; 62: 3120-3125; Henriksen G., Fisher D. R., Roeske J. C., et al., *Targeting of osseous sites with alpha-emitting 223Ra: comparison with the beta-emitter 89Sr in mice*, J. Nucl. Med 2003; 44: 252-59).
39. Lewington V. J., Bone-seeking radionuclides for therapy, J. Nucl. Med 2005; 46 (suppl 1): 38S-47S; Liepe K., *Alpharadin, a 223Ra-based alpha-particle-emitting pharmaceutical for the treatment of bone metastases in patients with cancer*, Curr. Opin. Investig. Drugs 2009; 10: 1346-58; McDevitt M. R., Sgouros G., Finn R. D., et al., *Radioimmunotherapy with alpha-emitting nuclides*, Eur. J. Nucl. Med. 1998; 25: 1341-51.
40. Kerr C., *(223)Ra targets skeletal metastases and spares normal tissue*, Lancet Oncol. 2002; 3: 453; Li Y., Russell P. J., Allen B. J., *Targeted alpha-therapy for control of micrometastatic prostate cancer*, Expert Rev. Anticancer Ther. 2004; 4: 459-68.

The invention claimed is:
1. A pharmaceutical combination comprising:
component A, which is 2-amino-N-[7-methoxy-8-(3-morpholin-4-ylpropoxy)-2,3-dihydroimidazo[1,2-c]quinazolin-5-yl]pyrimidine-5-carboxamide,
or a physiologically acceptable salt, solvate, hydrate or stereoisomer thereof; and
component B, which is radium-223 dichloride.

2. The pharmaceutical combination according to claim 1, wherein component A is
    2-amino-N-[7-methoxy-8-(3-morpholin-4-ylpropoxy)-2,3-dihydroimidazo[1,2-c]quinazolin-5-yl]pyrimidine-5-carboxamide,
    or a physiologically acceptable salt thereof.

3. The pharmaceutical combination according to claim 1, wherein component A is
    2-amino-N-[7-methoxy-8-(3-morpholin-4-ylpropoxy)-2,3-dihydroimidazo[1,2-c]quinazolin-5-yl]pyrimidine-5-carboxamide dihydrochloride.

4. The pharmaceutical combination according to claim 1, wherein component A is
    2-amino-N-[7-methoxy-8-(3-morpholin-4-ylpropoxy)-2,3-dihydroimidazo[1,2-c]quinazolin-5-yl]pyrimidine-5-carboxamide.

5. A method for treatment of hepatocyte carcinoma, lung cancer, non-small cell lung carcinoma, colorectal cancer, melanoma, pancreatic cancer, prostate cancer, breast cancer or metastases thereof, comprising administering to a patient in need thereof a therapeutically effective amount of the pharmaceutical combination according to claim 1.

6. A kit comprising the pharmaceutical combination according to claim 1, and optionally one or more further pharmaceutical agents C,
    wherein optionally both or either of components A and B are in the form of a pharmaceutical formulation which is ready for use to be administered simultaneously, concurrently, separately or sequentially.

7. A pharmaceutical composition comprising the pharmaceutical combination according to claim 1 and a pharmaceutically acceptable ingredient.

8. A method for treatment of multiple myeloma, lung cancer, breast cancer, prostate cancer, or metastases thereof, comprising administering to a patient in need thereof a therapeutically effective amount of the pharmaceutical combination according to claim 1.

9. The method according to claim 5, wherein the metastases are bone metastases.

10. The method of claim 8, wherein the prostate cancer is castration-resistant prostate cancer (CRPC).

11. The method of claim 5, wherein the pharmaceutical combination comprises
    2-amino-N-[7-methoxy-8-(3-morpholin-4-ylpropoxy)-2,3-dihydroimidazo[1,2-c]quinazolin-5-yl]pyrimidine-5-carboxamide
    or a physiologically acceptable salt thereof.

12. The kit of claim 6, wherein the pharmaceutical combination comprises
    2-amino-N-[7-methoxy-8-(3-morpholin-4-ylpropoxy)-2,3-dihydroimidazo[1,2-c]quinazolin-5-yl]pyrimidine-5-carboxamide
    or a physiologically acceptable salt thereof.

13. The pharmaceutical composition of claim 7, wherein the pharmaceutical combination comprises
    2-amino-N-[7-methoxy-8-(3-morpholin-4-ylpropoxy)-2,3-dihydroimidazo[1,2-c]quinazolin-5-yl]pyrimidine-5-carboxamide
    or a physiologically acceptable salt thereof.

14. The method of claim 8, wherein the pharmaceutical combination comprises
    2-amino-N-[7-methoxy-8-(3-morpholin-4-ylpropoxy)-2,3-dihydroimidazo[1,2-c]quinazolin-5-yl]pyrimidine-5-carboxamide
    or a physiologically acceptable salt thereof.

* * * * *